United States Patent
Burton et al.

(10) Patent No.: US 6,376,170 B1
(45) Date of Patent: *Apr. 23, 2002

(54) LIGAND CAPTURE-DIRECTED SELECTION OF ANTIBODY

(75) Inventors: Dennis R. Burton, La Jolla; Roberto Burioni; R. Anthony Williamson, both of Del Mar; Pietro P. Sanna, San Diego, all of CA (US)

(73) Assignee: The Scripps Research Institute, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/972,564

(22) Filed: Nov. 18, 1997

Related U.S. Application Data

(63) Continuation of application No. 08/316,914, filed on Oct. 3, 1994, now abandoned.

(51) Int. Cl.[7] .................................................. C12Q 1/70
(52) U.S. Cl. ........................... 435/5; 435/7.91; 436/518
(58) Field of Search ..................... 435/5, 7.91; 436/518

(56) References Cited

U.S. PATENT DOCUMENTS 4,486,530 A * 12/1984 David et al. ............... 435/7.91
4,514,505 A * 4/1985 Canfield et al.
5,126,130 A * 6/1992 Lussenhop et al.
5,272,059 A * 12/1993 Schlaeppi et al. ........... 435/7.9

OTHER PUBLICATIONS

Odell et al., Two Monoclonal Antibody "Sandwich"–Type Assay of Human Lutropin, with No Cross Reaction with Choriogonadotropin, Clin. Chem. 33/9: 1603–1607, 1987.*

Williamson et al., "Human monoclonal antibodies against a plethora of viral pathogens from single combinatorial libraries," Proc. Natl. Acad. Sci. USA, 90:4141–4145, 1993.*

* cited by examiner

Primary Examiner—Donna C. Wortman
(74) Attorney, Agent, or Firm—Fish & Richardson P.C.

(57) ABSTRACT

The present invention provides a novel method for the identification and clonal isolation of antibodies that bind to unique epitopes. The method is based on the use of antibodies as solid phase capture reagents to bind a known capture antibody epitope, thereby precluding the capture antibody epitope from being presented to a population of antibodies to be screened. The method is particularly suited for screening libraries of cloned antibodies, such as phage display combinatorial antibodies. An antibody specific for herpes simplex virus (HSV), was employed as a model for the assay.

9 Claims, 5 Drawing Sheets

LIGAND CAPTURE-DIRECTED SELECTION OF ANTIBODY

This is a continuation of application Ser. No. 08/316,914, filed Oct. 3, 1994, now abandoned.

BACKGROUND OF THE INVENTION

1. Field of the Invention

The present invention relates generally to immunological assay techniques and specifically to a method for identifying an antibody that binds to a novel epitope through the use of solid-phase capture reagents that bind antigen at a preselected epitope and panning of a combinatorial library.

2. Description of Related Art

Generally, any preparation of polyclonal or monoclonal antibodies can be used as a source of antibody molecules for cloning purposes. The use of filamentous phage display vectors, referred to as phagemids, has been repeatedly shown to allow the efficient preparation of large libraries of monoclonal antibodies having diverse and novel immunospecificites. The technology uses a filamentous phage coat protein membrane anchor domain as a means for linking gene-product and gene during the assembly of filamentous phage replication, and has been used for the cloning and expression of antibodies from combinatorial libraries (Kang, et al, *Proc. Natl. Acad. Sci.*, U.S.A., 88:4363, 1991). Combinatorial libraries of antibodies have been produced using both the cpVIII membrane anchor and the cpIII membrane anchor (Barbas, et al, *Proc. Natl. Acad. Sci.*, U.S.A., 88:7978, 1991).

The diversity of a phagemid library can be manipulated to increase and/or alter the immunospecificities of the monoclonal antibodies of the library to produce and subsequently identify additional, desirable, human monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable immunoreaction and neutralization capabilities.

Since its conception just a few years ago, the combinatorial approach has allowed unprecedented access to the human antibody response. The cloning of antibodies from preimmune, immune, and memory compartments of the human immune system has been demonstrated. Combinatorial antibodies have been shown to provide an accurate functional reflection of the natural response as demonstrated by the ability of cloned antibodies to compete with serum antibodies for binding antigens.

Modification of the techniques that are useful in standard immunoassays can be employed for cloning unique antibodies. Immunologic assays for the detection of antigenic substances or antibodies in specimens are well known in the art. Immunoassays fall into two main categories. First, there are those immunoassays wherein one of the binding pair, either an antigen or an antibody, is attached to a solid phase, and a second binding partner, which is labeled, usually an antibody, is in the liquid phase. If the specimen contains the substance to be detected, then a complex is formed composed of the solid phase first binding partner, the substance being detected, and the detectably labeled second binding partner. In the second category are those immunoassays wherein the first and second binding partners both react freely in the liquid phase to form an immune complex if the specimen contains the substance to be detected. This immune complex is then removed from the liquid phase by binding of one of the binding partners to a carrier which is modified such that is will bind the immune complex.

An example of a sandwich immunoassay is described in David, et al., (U.S. Pat. No. 4,376,110). The assay disclosed here uses two different monoclonal antibodies from two different hybridomas. The David technique involves one of the monoclonal antibodies being bound to the solid phase throughout the assay, rather than being used in a homogeneous phage. The solid phase monoclonal antibody 1 is reacted with the liquid phase to detect the possible presence of antigen. A monoclonal antibody 2, which is labeled and soluble in liquid phase, will form, in the presence of antigen, a sandwich between solid phase monoclonal antibody 1, antigen, and labeled monoclonal antibody 2.

In Gallati, et al., United Kingdom Patent GB No. 2,074,727B, sandwich assays are described which may occur in liquid phase between (1) two monoclonal antibodies specific for two different epitopes of the same antigen, (2) a monoclonal antibody and polyclonal antibodies raised in another species to the same antigen, and (3) polyclonal antibodies raised in two different species and being directed towards different epitopes of the same antigen.

In Milich, et al., (WO 94/08597), anti-peptide antibodies are utilized as solid-phase capture reagents to bind antigen which is complexed to serum antibodies. The bound serum antibody is then detected with a labelled second antibody. In Curtis (U.S. Pat. No. 5,126,240), a first monoclonal antibody is bound to a solid matrix to form a solid support prior to formation of an admixture containing antigen. The presence of a solid phase-bound immunoreactant is then determined by the use of a second monoclonal antibody molecule.

In contrast to the present invention, standard immunoassays are utilized for the detection of the presence of antigen, antibody, or both. With its ability to provide large numbers of human antibodies directed against a single antigen, the combinatorial approach allows for the rapid assessment of immunodominant as well as neutralizing epitopes in the context of the human response. There remains a need for identifying and subsequently cloning antibodies that specifically bind to antigens known to be important targets for neutralizing antibodies, for example, even when a recombinant or purified form of the antigen is unavailable. The present invention provides a simple, high-sensitivity technique directed toward panning a population of antibody molecules, preferably in a phage display combinatorial library, in order to identify and clone antibody molecules that bind to a number of virus-neutralizing or other unknown epitopes.

SUMMARY OF THE INVENTION

The present invention provides a novel and simple "antigen-capture" technique to more accurately select antibody molecules, e.g., Fab, specifically binding to antigens known to be important targets for neutralizing antibodies, for example. Antibody specific for a preselected epitope, such as a non-neutralizing epitope of a desired antigen, is attached to a solid surface and used to "capture" the antigen. After unbound material is washed away, a panning procedure is performed over the captured or masked antigen to identify antibodies that bind to unmasked antigens. The method of the invention is particularly useful for crude cell or viral lysates containing antigens of interest and for panning using phage display combinatorial libraries.

Thus the invention provides a method for identifying an antibody molecule that binds to an unmasked epitope on a preselected antigen, having a preselected first epitope and at least one additional epitope, comprising the steps of: a) contacting the preselected antigen having the preselected first epitope, with a first antibody molecule, under conditions which allow the first epitope of the antigen to bind to the first antibody body molecule and form an immunocomplex; b) contacting a second antibody molecule with the immunocomplex such that the second antibody molecule binds to a second, unmasked epitope on the antigen; and c) removing the second antibody molecule bound to the second epitope. Following step c), any phage, for example, expressing a second antibody molecule on its surface which binds to a second epitope, is clonally isolated and its DNA sequenced.

BRIEF DESCRIPTION OF THE DRAWINGS

FIG. 2 shows the neutralizing activity of Fab8, as measured by plaque reduction.

FIG. 4 shows a post-attachment neutralization assay. Fab8 reduced HSV-1 infectivity after virion attachment.

DETAILED DESCRIPTION OF THE INVENTION

Figure 1:
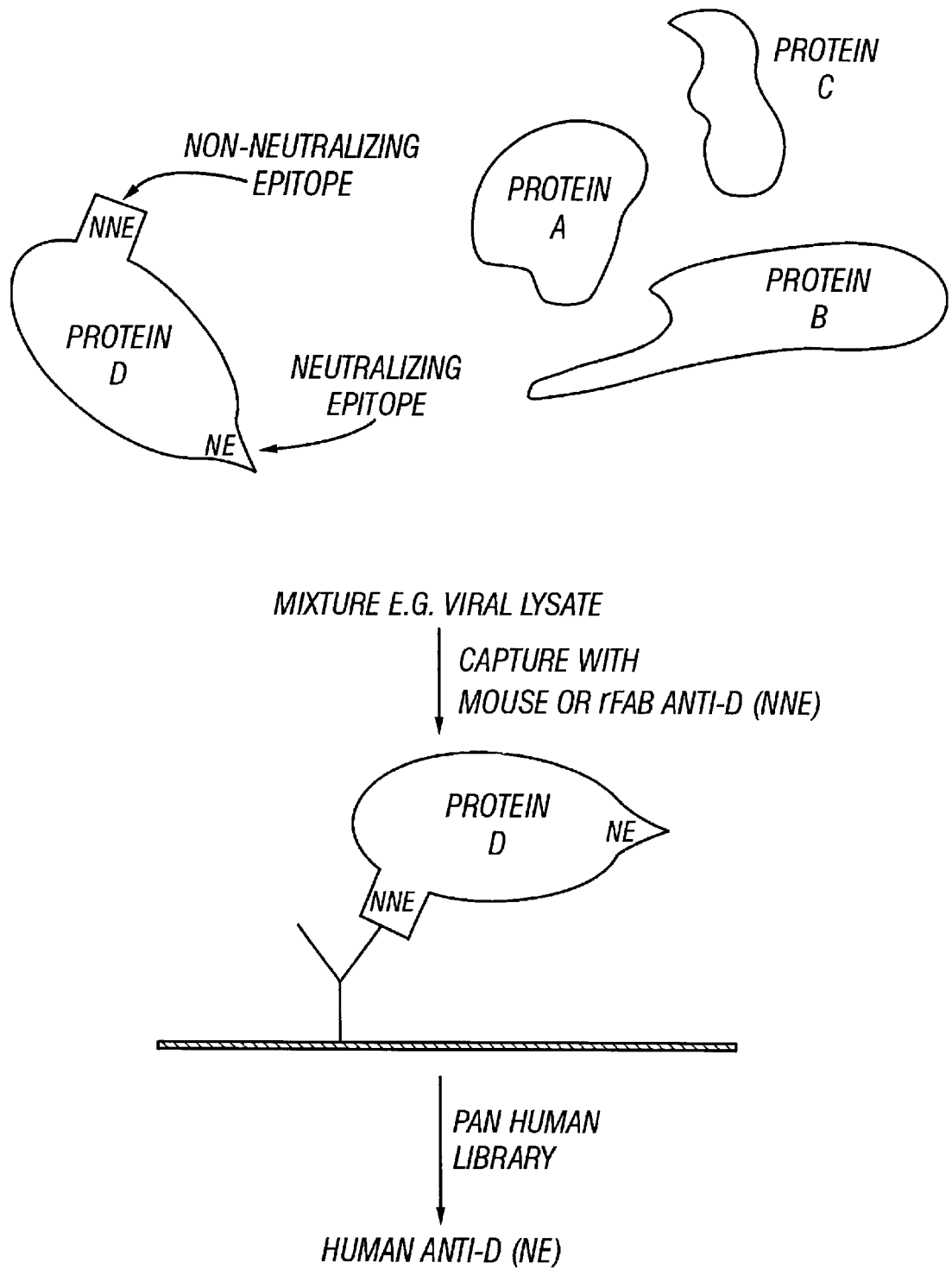
FIG. 1 is a schematic illustration of the "antigen-capture" technique using HSV glycoprotein D as a model.

The present invention provides a novel directed selection technique for identifying antibodies that bind to novel epitopes on a preselected antigen. In a preferred embodiment, the technique includes fixing an antibody that binds to a preselected antigen, to a solid support, and thereafter, adding the antigen to the bound antibody. The antigen is then "captured" by the bound antibody and other epitopes on the antigen are now available to bind to a population of second antibody molecules, for example, Fab in a phage display combinatorial library.

The term "antibody" or "antibody molecule" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference). Therefore, the phrase "antibody molecule" in its various forms as used herein contemplates both an intact antibody (immunoglobulin) molecule and an immunologically active portion of an antibody (immunoglobulin) molecule.

The term "monoclonal antibody" refers to a population of one species of antibody molecule of determined (known) antigen-specificity. A monoclonal antibody contains only one species of antibody combining site capable of immunoreacting with a particular antigen and thus typically displays a single binding affinity for that antigen. A monoclonal antibody may therefore contain a bispecific antibody molecule having two antibody combining sites, each immunospecific for a different antigen. Preferably, the first antibody molecule affixed to a solid support in the method of the invention is a monoclonal antibody. In addition, the antibody molecules in a phage display combinatorial library are also monoclonal antibodies.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The word "complex" as used herein refers to the product of a specific binding agent-ligand reaction. An exemplary complex is an immunoreaction product formed by an antibody-antigen reaction.

The term "antigen" refers to a polypeptide or protein that is able to specifically bind to (immunoreact with) an antibody and form an immunoreaction product (immunocomplex). The site on the antigen with which the antibody binds is referred to as an antigenic determinant or epitope.

In a first embodiment, the invention provides a method for identifying an antibody molecule that binds to an unmasked epitope on a preselected antigen, having a preselected first epitope and at least one additional epitope, comprising the steps of: a) contacting the preselected antigen having the preselected first epitope, with a first antibody molecule, under conditions which allow the first epitope of the antigen to bind to the first antibody molecule and form an immunocomplex; b) contacting a second antibody molecule with the immunocomplex such that the second antibody molecule binds to a second, unmasked epitope on the antigen; and c) removing the second antibody molecule bound to the second epitope. Preferably, the second antibody molecule in the method of the invention is in a phage display combinatorial library. Therefore, following step c), removing or collecting the second antibody molecule that is bound, any phage, for example, expressing a second antibody molecule on its surface which binds to a second epitope, is clonally isolated and its DNA sequenced according to common methods known to those of skill in the art.

The method of the invention for detection of antibodies that bind to novel epitopes in a sample is performed in vitro, for example, in immunoassays in which the antibodies can be identified in liquid phase or bound to a solid phase carrier. Preferably, the method is performed with a capture antibody bound to a solid support. Most preferably, the capture antibody is a monoclonal antibody molecule.

Examples of types of immunoassays which can be utilized to detect novel antibodies in a sample, include competitive and non-competitive immunoassays in either a direct or indirect format. Examples of such immunoassays are the radioimmunoassay (RIA) and the sandwich (immunometric) assay. Detection of the antibodies can be done utilizing immunoassays which are run in either the forward, reverse, or simultaneous modes, including competition immunoassays and immunohistochemical assays on physiological samples. Preferably, the method of the invention utilizes a forward immunoassay. Those of skill in the art will know, or can readily discern, other immunoassay formats without undue experimentation.

Solid phase-bound antibody molecules are bound by adsorption from an aqueous medium, although other modes of affixation, such as covalent coupling or other well known means of affixation to the solid matrix can be used. Preferably, the first antibody molecule is bound to a support before forming an immunocomplex with antigen, however, the immunocomplex can be formed prior to binding the complex to the solid support.

Non-specific protein binding sites on the surface of the solid phase support are preferably blocked. After adsorption of solid phase-bound antibodies, an aqueous solution of a protein free from interference with the assay such as bovine, horse, or other serum albumin that is also free from contamination with the antigen is admixed with the solid phase to adsorb the admixed protein onto the surface of the antibody—containing solid support at protein binding sites on the surface that are not occupied by the antibody molecule.

A typical aqueous protein solution contains about 2–10 weight percent bovine serum albumin in PBS at a pH of about 7–8. The aqueous protein solution-solid support mixture is typically maintained for a time period of at least one hour at a temperature of about 4°–37° C. and the resulting solid phase is thereafter rinsed free of unbound protein.

The first preselected antibody can be bound to many different carriers and used to detect novel epitope binding antibodies in a sample. Examples of well-known carriers include glass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation.

In addition, if desirable, an antibody for detection in these immunoassays can be detectably labeled in various ways. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the antibodies used in the method of the invention can be done using standard techniques common to those of ordinary skill in the art.

For purposes of the invention, antibodies that bind to a second, unmasked antigen may be detected using any sample containing a detectable amount of antigen can be used. A sample can be a liquid such as urine, saliva, cerebrospinal fluid, blood, serum and the like. A sample can also be a cell lysate, viral lysate or other crude, semi-purified, or purified antigen preparation.

The preselected antigen can be any antigen such as a bacterial, viral, parasitic, fungal, tumor and self-antigen. Examples of viral antigens include antigens derived from viruses selected from the group consisting of hepatitis B virus (HBV), human immunodeficiency virus (HIV), influenza A virus, Epstein Barr virus (EBV), herpes simplex virus (HSV), respiratory syncytial virus (RSV), human cytomegalovirus (HCMV), varicella zoster virus (VZV), and measles virus. For exemplary purposes, the HSV glycoprotein D antigen is illustrated herein (FIG. 1) as the preselected antigen.

Once a preselected antigen is "captured" by a first antibody bound or to be bound to a solid support, unbound antigen is washed away, and antibody molecules of interest can be panned to identify those antibody molecules which bind to an "unmasked" epitope on the antigen. As used herein, the term "unmasked" refers to an epitope that is free to bind to a second antibody and is not bound by a first preselected antibody. For example, when it is desirable to identify a neutralizing epitope on a viral antigen, the preselected antibody and the corresponding preselected first epitope will be a non-neutralizing epitope, leaving any neutralizing epitopes "unmasked" or free to react with a corresponding neutralizing antibody.

The specific concentrations of the antibody and antigen, the temperature and time of incubation, as well as other assay conditions, can be varied, depending on such factors as the concentration of the antigen in the sample, the nature of the sample and the like. Those of skill in the art will be able to determine operative and optimal assay conditions for each determination by employing routine experimentation.

For example, the immunoassay may be run at 4°–45° C., and preferably at about 15°–37° C. Each incubation step may be as long as 72 hours. Other steps such as washing, stirring, shaking, filtering, or pre-assay extraction of antigen, and the like, may, of course be added to the assay, as may be desired or necessary for a particular situation.

Although any preparation containing a mixture of antibodies or antibody molecules can be utilized as a source of the second antibody, preferably, a combinatorial library is used, and most preferably, a phage display library as described in Barbas, et al., (Combinatorial immunoglobulin libraries on the surface of phage (Phabs): Rapid selection of antigen-specific Fabs., Methods: *A Companion to Methods in Enzymol.*, (Lerner and Burton, eds), vol.2, pp.119–124, Academic Press, Orlando, 1991; Barbas, et al, *Proc. Natl. Acad. Sci.*, U.S.A. 88:7978, 1991), incorporated herein by reference. (See also for reference purposes, Huse, et al., *Science*, 246:1275–1281, 1989).

As a working model to illustrate the "capture" technique, the present invention describes a method for identifying novel HSV-neutralizing human monoclonal antibodies. One of skill in the art could now identify a variety of novel antibody molecules using the exemplified model. Virtually any antibody can be identified that is distinct from the preselected antibody (which binds to the preselected epitope). The methods are based generally on the use of combinatorial libraries of antibody molecules which can be produced from a variety of sources, and include naive libraries, modified libraries, and libraries produced directly from donors, for example, as exemplified herein, human donors exhibiting an HSV-specific immune response.

The combinatorial library production and manipulation methods have been extensively described in the literature, and will not be reviewed in detail herein, except for those features required to make and use unique embodiments of the present invention. However, the methods generally involve the use of a filamentous phage (phagemid) surface expression vector system for cloning and expressing antibody species of the library. Various phagemid cloning systems to produce combinatorial libraries have been described by others. See, for example the preparation of combinatorial antibody libraries on phagemids as described by Kang, et al., *Proc. Natl. Acad. Sci.*, USA, 88:4363–4366 (1991); Barbas, et al, *Proc. Natl. Acad. Sci.*, USA, 88:7978–7982 (1991); Zebedee, et al., *Proc. Natl. Acad. Sci.*, USA, 89:3175–3179 (1992); Kang, et al, *Proc. Natl. Acad. Sci.*, USA, 88:11120–11123 (1991); Barbas, et al, *Proc. Natl. Acad. Sci.*, USA, 89:4457–4461 (1992); and Gram, et al, *Proc. Natl. Acad. Sci.*, USA, 89:3576–3580 (1992), which references are hereby incorporated by reference.

In the working Example described for illustrative purposes herein, the method involves preparing a phagemid library of human monoclonal antibodies by using donor immune cell messenger RNA from HSV-infected donors. The donors can be symptomatic of a HSV infection, but the donor can also be asymptomatic, as the resulting library contains a substantially higher number of HSV-neutralizing human monoclonal antibodies. Additionally, because HSV infection is often associated with other diseases, the patient may optionally present substantial symptoms of one or more other diseases typically associated with symptomatic or asymptomatic HSV infection, notably AIDS, as demonstrated by the library utilized herein. Those of skill in the art will be able to use the working example as a model for identifying other various desired antibody molecules.

In another example, the donor is naive relative to a conventional immune response to the antigen, e.g. HSV, (i.e. the donor is not HSV-infected, and yet antibodies in the donor cross-react with one or more HSV antigens). Alternatively, the library can be synthetic, or can be derived from a donor who has an immune response to other antigens. The source of the nucleic acid used for preparation of a library to be panned in the method of the invention will vary depending on the preselected antigen and the antibody desired to be identified.

The method for producing a human monoclonal antibody generally involves (1) preparing separate H and L chain-encoding gene libraries in cloning vectors using human immunoglobulin genes as a source for the libraries, (2) combining the H and L chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected antigen, thereby isolating one or more species of phagemid containing particular H and L chain-encoding genes and antibody molecules that immunoreact with the preselected antigen.

As a further characterization of the present invention the nucleotide and corresponding amino acid residue sequence of the antibody molecule's H or L chain encoding gene is determined by nucleic acid sequencing. The primary amino acid residue sequence information provides essential information regarding the antibody molecule's epitope reactivity.

Sequence comparisons of identified immunoreactive monoclonal antibody variable chain region sequences are aligned based on sequence homology, and groups of related antibody molecules are identified in which heavy chain or light chain genes share substantial sequence homology.

An exemplary preparation of a human monoclonal antibody is described in the Examples. The isolation of a particular vector capable of expressing an antibody of interest involves the introduction of the dicistronic expression vector into a host cell permissive for expression of filamentous phage genes and the assembly of phage particles. Where the binary vector system is used, both vectors are introduced in the host cell. Typically, the host is *E. coli*. Thereafter, a helper phage genome is introduced into the host cell containing the immunoglobulin expression vector (s) to provide the genetic complementation necessary to allow phage particles to be assembled. The resulting host cell is cultured to allow the introduced phage genes and immunoglobulin genes to be expressed, and for phage particles to be assembled and shed from the host cell. The shed phage particles are then harvested (collected) from the host cell culture media and screened for desirable immunoreaction and neutralization properties.

The harvested particles are "panned" for immunoreaction with a preselected antigen. For example, in the method of the invention, the preselected antigen, such as a virus, is bound to a solid phase via an antibody specific for the antigen wherein the antibody is first attached to the solid phase before the particles are panned. The strongly immunoreactive particles are then collected, and individual species of particles are clonally isolated and further screened for immunoreactivity, or as exemplified herein, HSV neutralization. Phage which produce neutralizing antibodies, for example, are selected and used as a source of a human HSV neutralizing monoclonal antibody.

Because an immunoaffinity isolated antibody composition includes phage particles containing surface antibody, one embodiment involves the manipulation of the resulting cloned genes to truncate the immunoglobulin-coding gene such that a soluble Fab fragment is secreted by the host *E*.

*coli* cell containing the phagemid vector rather than the production of a phagemid having surface antibody. Thus, the resulting manipulated cloned immunoglobulin genes produce a soluble Fab which can be readily characterized in ELISA assays for epitope binding studies, in competition assays with antibody molecules of known epitopic specificity, and in functional assays, such as neutralization assays for example. The solubilized Fab provides a reproducible and comparable antibody preparation for comparative and characterization studies.

The preparation of soluble Fab is generally described in the immunological arts, and can be conducted as described herein in the Examples, or as described by Burton, et al., *Proc. Natl. Acad. Sci.*, USA, 88:10134–10137 (1991). The preparation of human monoclonal antibodies of this invention depends, in one embodiment, on the cloning and expression vectors used to prepare the combinatorial antibody libraries described herein. The cloned immunoglobulin heavy and light chain genes can be shuttled between lambda vectors, phagemid vectors and plasmid vectors at various stages of the methods described herein.

The phagemid vectors produce fusion proteins that are expressed on the surface of an assembled filamentous phage particle. A preferred phagemid vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide defining an immunoglobulin heavy or light chain variable region, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface. The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from Erwinia carotova are described in Lei, et al., (Nature, 331:543–546, 1988).

The leader sequence of the pelB protein has previously been used as a secretion signal for fusion proteins. Better, et al., *Science*, 240:1041–1043 (1988); Sastry, et al., *Proc. Natl. Acad. Sci.*, USA, 86:5728–5732 (1989); and Mullinax, et al., *Proc. Natl. Acad. Sci.*, USA, 87:8095–8099 (1990). Amino acid residue sequences for other secretion signal polypeptide domains from *E. coli* useful in this invention as described in Oliver, (*Escherichia coli* and *Salmonella typhimurium*, Neidhard, F. C. (ed.), American Society for Microbiology, Washington, D.C., 1:56–69, 1987).

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52 (Ohkawa, et al., *J. Biol. Chem.*, 256:9951–9958, 1981). An exemplary membrane anchor would consist of residues 26 to 40 of cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage atone end of the phage particle with typically about 4 to 6 copies of the coat protein.

For detailed descriptions of the structure of filamentous phage particles, their coat proteins and particle assembly, see the reviews by Rached, et al., *Microbiol. Rev.*, 50:401–427 (1986); and Model, et al., in "The Bacteriophages: Vol. 2", R. Calendar, ed. Plenum Publishing Co., pp. 375–456 (1988).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3–9 nucleotides long located 3–11 nucleotides upstream from the initiation codon (Shine, et al., *Nature*, 254:34 (1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors:

(i) The degree of complementarity between the SD sequence and 3' end of the 16S rRNA.

(ii) The spacing and possibly the DNA sequence lying between the SD sequence and the AUG. Roberts, et al., *Proc. Natl. Acad. Sci.*, USA, 76:760, (1979a); Roberts, et al., *Proc. Natl. Acad. Sci.* USA, 76:5596 (1979b); Guarente, et al., *Science*, 209:1428 (1980); and Guarente, et al., *Cell*, 20:543 (1980). Optimization is achieved by measuring the level of expression of genes in plasmids in which this spacing is systematically altered. Comparison of different mRNAs shows that there are statistically preferred sequences from positions −20 to +13 (where the A of the AUG is position 0). Gold, et al., *Annu. Rev Microbiol.*, 35:365 (1981). Leader sequences have been shown to influence translation dramatically. Roberts, et al., 1979a, b supra.

(iii) The nucleotide sequence following the AUG, which affects ribosome binding. Taniguchi, et al., *J. Mol. Biol.*, 118:533 (1978). The 3' control sequences define at least one termination (stop) codon in frame with and operatively linked to the heterologous fusion polypeptide.

In preferred embodiments, the vector utilized includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is i E. coli.For use of a vector in *E. coli,* a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook, et al., in "Molecular Cloning: a Laboratory Manual", 2nd edition, Cold Spring Harbor Laboratory Press (1989).

The ColE1 and p15A replicons are particularly preferred for use in one embodiment of the present invention where two "binary" plasmids are utilized because they each have the ability to direct the replication of plasmid in *E. coli* while the other replicon is present in a second plasmid in the same *E. coli* cell. In other words, ColE1 and p15A are non-interfering replicons that allow the maintenance of two plasmids in the same host (see, for example, Sambrook, et al., supra, at pages 1.3–1.4). This feature is particularly important in the binary vectors embodiment of the present invention because a single host cell permissive for phage replication must support the independent and simultaneous replication of two separate vectors, namely a first vector for expressing a heavy chain polypeptide, and a second vector for expressing a light chain polypeptide.

In addition, those embodiments that include a prokaryotic replicon can also include a gene whose expression confers a selective advantage, such as drug resistance, to a bacterial host transformed therewith. Typical bacterial drug resistance genes are those that confer resistance to ampicillin, tetracycline, neomycin/kanamycin or cholamphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

A vector for expression of a monoclonal antibody of the invention on the surface of a filamentous phage particle is a recombinant DNA (rDNA) molecule adapted for receiving and expressing translatable first and second DNA sequences in the form of first and second polypeptides wherein one of the polypeptides is fused to a filamentous phage coat protein membrane anchor. That is, at least one of the polypeptides is a fusion polypeptide containing a filamentous phage membrane anchor domain, a prokaryotic secretion signal domain, and an immunoglobulin heavy or light chain variable domain.

A DNA expression vector for expressing a heterodimeric antibody molecule provides a system for independently cloning (inserting) the two translatable DNA sequences into two separate cassettes present in the vector, to form two separate cistrons for expressing the first and second polypeptides of the antibody molecule, or the ligand binding portions of the polypeptides that comprise the antibody molecule (i.e., the H and L variable regions of an immunoglobulin molecule). The DNA expression vector for expressing two cistrons is referred to as a dicistronic expression vector.

The vector comprises a first cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage membrane anchor as defined herein. The cassette preferably includes DNA expression control sequences for expressing the receptor polypeptide that is produced when an insert translatable DNA sequence (insert DNA) is directionally inserted into the cassette via the sequence of nucleotides adapted for directional ligation. The filamentous phage membrane anchor is preferably a domain of the cpIII or cpVIII coat protein capable of binding the matrix of a filamentous phage particle, thereby incorporating the fusion polypeptide onto the phage surface.

The receptor expressing vector also contains a second cassette for expressing a second receptor polypeptide. The second cassette includes a second translatable DNA sequence that encodes a secretion signal, as defined herein, operatively linked at its 3' terminus via a sequence of nucleotides adapted for directional ligation to a downstream DNA sequence of the vector that typically defines at least one stop codon in the reading frame of the cassette. The second translatable DNA sequence is operatively linked at its 5' terminus to DNA expression control sequences forming the 5' elements. The second cassette is capable, upon insertion of a translatable DNA sequence (insert DNA), of expressing the second fusion polypeptide comprising a receptor of the secretion signal with a polypeptide coded by the insert DNA.

An upstream translatable DNA sequence encodes a prokaryotic secretion signal as described earlier. The upstream translatable DNA sequence encoding the pelB secretion signal is a preferred DNA sequence for inclusion in a receptor expression vector. A downstream translatable DNA sequence encodes a filamentous phage membrane anchor as described earlier. Thus, a downstream translatable DNA sequence encodes an amino acid residue sequence that corresponds, and preferably is identical, to the membrane anchor domain of either a filamentous phage gene III or gene VIII coat polypeptide.

A cassette in a DNA expression vector of this invention is the region of the vector that forms, upon insertion of a translatable DNA sequence (insert DNA), a sequence of nucleotides capable of expressing, in an appropriate host, a fusion polypeptide. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

Thus, a DNA expression vector for expressing an antibody molecule provides a system for cloning translatable DNA sequences into the cassette portions of the vector to produce cistrons capable of expressing the first and second polypeptides, i.e., the heavy and light chains of a monoclonal antibody.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see, for example, Rasched, et al., Microbiol. Rev., 50:401–427 (1986); and Horiuchi, J. Mol. Biol., 188:215–223 (1986)).

A preferred filamentous phage origin of replication for use in the present invention is an M13, f1 or fd phage origin of replication (Short, et al., Nucl. Acids Res., 16:7583–7600 (1988)). Preferred DNA expression vectors for cloning and expression a human monoclonal antibody of this invention are the dicistronic expression vectors pCOMB8, pCOMB2-8, pCOMB3, pCOMB2-3 and pCOMB2-3', described herein.

It is to be understood that, due to the genetic code and its attendant redundancies, numerous polynucleotide sequences can be designed that encode a contemplated heavy or light chain immunoglobulin variable region amino acid residue sequence. Thus, the invention contemplates such alternate polynucleotide sequences incorporating the features of the redundancy of the genetic code.

The following examples are intended to illustrate but not limit the invention. While they are typical of those that might be used, other procedures known to those skilled in the art may alternatively be used.

EXAMPLE 1

Construction of a Dicistronic Expression Vector for Producing a Heterodimeric Receptor on Phage Particles To obtain a vector system for generating a large number of Fab antibody fragments that can be screened directly, expression libraries in bacteriophage Lambda have previously been constructed as described in Huse, et al. (Science, 246:1275–1281, 1989). However, these systems did not contain design features that provide for the expressed Fab to be targeted to the surface of a filamentous phage particle as described by Barbas, et al. (Proc. Natl. Acad. Sci. USA, 33:7978–7982, 1991).

The main criterion used in choosing a vector system is the necessity of generating the largest number of Fab fragments which could be screened directly. Bacteriophage Lambda was selected as the starting point to develop an expression vector for three reasons. First, in vitro packaging of phage DNA was the most efficient method of reintroducing DNA into host cells. Second, it was possible to detect protein expression at the level of single phage plaques. Finally, the screening of phage libraries typically involved less difficulty with nonspecific binding. The alternative, plasmid cloning vectors, are only advantageous in the analysis of clones after they have been identified. This advantage was not lost in the present system because of the use of a dicistronic expression vector such as pCombVIII, thereby permitting a plasmid containing the heavy chain, light chain, or Fab expressing inserts to be excised.

a. Construction of Dicistronic Expression Vector pCOMB
(i) Preparation of Lambda Zap™ II Lambda Zap™ II is a derivative of the original Lambda Zap (ATCC #40,298) that maintains all of the characteristics of the original Lambda Zap including 6 unique cloning sites, fusion protein expression, and the ability to rapidly excise the insert in the form of a phagemid (Bluescript SK-), but lacks the SAM 100 mutation, allowing growth on many Non-Sup F strains, including XL1-Blue. The Lambda Zap™ II was constructed as described in Short, et al. (Nuc. Acids Res., 16:7583–7600, 1988), by replacing the lambda S gene contained in a 4254 base pair (bp) DNA fragment produced by digesting lambda Zap with the restriction enzyme Nco 1. This 4254 bp DNA fragment was replaced with the 4254 bp DNA fragment containing the Lambda S gene isolated from Lambda gt10 (ATCC #40,179) after digesting the vector with the restriction enzyme Nco 1. The 4254 bp DNA fragment isolated from lambda gt10 was ligated into the original lambda Zap vector using T4 DNA ligase and standard protocols such as those described in Current Protocols in Molecular Biology, Ausubel, et al., eds., John Wiley and Sons, NY 1987, to form Lambda Zap™ II.

(ii) Preparation of Lambda Hc2

To express a plurality of $V_H$-coding DNA homologs in an E.coli host cell, a vector designated Lambda Hc2 was constructed. The vector provided the following: the capacity to place the $V_H$-coding DNA homologs in the proper reading frame; a ribosome binding site as described by Shine, et al. (Nature, 254:34, 1975); a leader sequence directing the expressed protein to the periplasmic space designated the pelB secretion signal; a polynucleotide sequence that coded for a known epitope (epitope tag); and also a polynucleotide that coded for a spacer protein between the $V_H$-coding DNA homolog and the polynucleotide coding for the epitope tag. Lambda Hc2 has been previously described by Huse, et al. (*Science,* 246:1274–1281, 1989).

To prepare Lambda Hc2, a synthetic DNA sequence containing all of the above features was constructed by designing single stranded polynucleotide segments of 20–40 bases that would hybridize to each other and form the double stranded synthetic DNA sequence. The individual single-stranded polynucleotide segments are shown in Table 1.

Polynucleotides N2, N3, N9-4, N11, N10-5, N6, N7 and N8 (Table 1) were kinased by adding 1 μl of each polynucleotide (0.1 μg/μl) and 20 units of $T_4$ polynucleotide kinase to a solution containing 70 mM Tris-HCl, pH 7.6, 10 mM $MgCl_2$, 5 mM dithiothreitol (DTT), 10 mM beta-mercaptoethanol, 500 micrograms per milliliter (μg/ml) bovine serum albumin (BSA). The solution was maintained at 37 degrees Centigrade (37° C.) for 30 minutes and the reaction stopped by maintaining the solution at 65° C. for 10 minutes. The two end polynucleotides, 20 mg of polynucleotides N1 and polynucleotides N12, were added to the above kinasing reaction solution together with 1/10 volume of a solution containing 20.0 mM Tris-HCl, pH 7.4, 2.0 mM $MgCl_2$ and 50.0 mM NaCl. This solution was heated to 70° C. for 5 minutes and allowed to cool to room temperature, approximately 25° C., over 1.5 hours in a 500 ml beaker of water. During this time period all 10 polynucleotides annealed to form a double stranded synthetic DNA insert. The individual polynucleotides were covalently linked to each other to stabilize the synthetic DNA insert by adding 40 μl of the above reaction to a solution containing 50 mM Tris-HCl, pH 7.5, 7 mM $MgCl_2$, 1 mM DTT 1 mM adenosine triphosphate (ATP) and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 μl of the above reaction, 4 μl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

aged according to the manufacture's instructions using Gigapack II Gold packing extract available from Stratagene, La Jolla, Calif. The packaged ligation mixture was plated on XL1-Blue cells (Stratagene). Individual Lambda plaques were cored and the inserts excised according to the in vivo excision protocol for Lambda Zap™ II provided by the manufacturer (Stratagene). This in vivo excision protocol moved the cloned insert from the Lambda Hc2 vector into a phagemid vector to allow for easy manipulation and sequencing. The accuracy of the above cloning steps was confirmed by sequencing the insert using the Sanger dideoxy method described in by Sanger, et al. (*Proc. Natl. Acad. Sci. USA,* 74:5463–5467, 1977), and using the manufacture's instructions in the AMV Reverse Transcriptase $^{35}$S-ATP sequencing kit (Stratagene).

(iii) Preparation of Lambda Lc2

To express a plurality of $V_L$-coding DNA homologs in an *E.coli* host cell, a vector designated Lambda Lc2 was constructed having the capacity to place the $V_L$-coding DNA homologs in the proper reading frame, provided a ribosome binding site as described by Shine, et al. (*Nature,* 254:34, 1975), provided the pelB gene leader sequence secretion signal that has been previously used to successfully secrete Fab fragments in *E.coli* by Lei, et al. (*J. Bac.,* 169:4379, 1987) and Better, et al. (*Science,* 240:1041, 1988), and also provided a polynucleotide containing a restriction endonuclease site for cloning. Lambda Lc2 has been previously described by Huse, et al. (*Science,* 246:1275–1281, 1989).

A synthetic DNA sequence containing all of the above features was constructed by designing single stranded polynucleotide segments of 20–60 bases that would hybridize to each other and form the double stranded synthetic DNA. The sequence of each individual single-stranded polynucleotide segment (1–8) within the double stranded synthetic DNA sequence is shown in Table 2.

Polynucleotides shown in Table 2 were kinased by adding 1 μl (0.1 μg/μl) of each polynucleotide and 20 units of $T_4$ polynucleotide kinase to a solution containing 70 mM Tris-HCl, pH 7.6, 10 mM MgCl, 5 mM DTT, 10 mM beta-mercaptoethanol, 500 mg/ml of BSA. The solution was maintained at 37° C. for 30 minutes and the reaction stopped by maintaining the solution at 65° C. for 10 minutes. The 20

TABLE 1

| N1) | 5' GGCCGCAAATTCTATTTCAAGGAGACAGTCAT 3' | (SEQ ID NO:1) |
|---|---|---|
| N2) | 5' AATGAAATACCTATTGCCTACGGCAGCCGCTGGATT 3' | (SEQ ID NO:2) |
| N3) | 5' GTTATTACTCGCTGCCCAACCAGCCATGGCCC 3' | (SEQ ID NO:3) |
| N6) | 5' CAGTTTCACCTGGGCCATGGCTGGTTGGG 3' | (SEQ ID NO:4) |
| N7) | 5' CAGCGAGTAATAACAATCCAGCGGCTGCCGTAGGCAATAG 3' | (SEQ ID NO:5) |
| N8) | 5' GTATTTCATTATGACTGTCTCCTTGAAATAGAATTTGC 3' | (SEQ ID NO:6) |
| N9-A) | 5' AGGTGAAACTGCTCGAGATTTCTAGACTAGTTACCCGTAC 3' | (SEQ ID NO:7) |
| N10-5) | 5' CGGAACGTCGTACGGGTAACTAGTCTAGAAATCTCGAG 3' | (SEQ ID NO:8) |
| N11) | 5' GACGTTCCGGACTACGGTTCTTAATAGAATTCG 3' | (SEQ ID NO:9) |
| N12) | 5' TCGACGAATTCTATTAAGAACCGTAGTC 3' | (SEQ ID NO:10) |

The completed synthetic DNA insert was ligated directly into the Lambda Zap™ II vector described in Example 1a(i) that had been previously digested with the restriction enzymes, Not I and Xho I. The ligation mixture was packng each of the two end polynucleotides, 01 and 08, were added to the above kinasing reaction solution together with 1/10 volume of a solution containing 20.0 mM Tris-HCl, pH 7.4, 2.0 mM MgCl and 15.0 mM sodium chloride (NaCl).

This solution was heated to 70° C. for 5 minutes and allowed to cool to room temperature, approximately 25° C., over 1.5 hours in a 500 ml beaker of water. During this time period all 8 polynucleotides annealed to form the double stranded synthetic DNA insert shown in FIG. 3. The individual polynucleotides were covalently linked to each other to stabilize the synthetic DNA insert by adding 40 µl of the above reaction to a solution containing 50 ml Tris-HCl, pH 7.5, 7 ml MgCl, 1 mm DTT 1 mm ATP and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

a pComb expression vector previously digested with Spe I and EcoR I. The proximity of the EcoR I restriction site to the 3' Spe I site, provided by the Lc2 vector, inhibited the complete digestion of the 3'Spe I site. Thus, digesting pComb with Spe I and EcoR I did not result in removal of the EcoR I site between the two Spe I sites.

The presence of a second Spe I restriction site may be undesirable for ligations into a pComb vector digested only with Spe I as the region between the two sites would be eliminated. Therefore, a derivative of Lambda Lc2 lacking the second or 3' Spe I site, designated Lambda Lc3, is produced by first digesting Lambda Lc2 with Spe I to form a linearized vector. The ends are filled in to form blunt ends which are ligated together to result in Lambda Lc3 lacking a Spe I site. Lambda Lc3 is a preferred vector for use in constructing a combinatorial vector as described below.

(iv) Preparation of pComb

Phagemids were excised from the expression vectors lambda Hc2 or Lambda Lc2 using an in vivo excision

TABLE 2

| | | |
|---|---|---|
| 1) | 5' TGAATTCTAAACTAGTCGCCAAGGAGACAGTCAT 3' | (SEQ ID NO: 11) |
| 2) | 5' AATGAAATACCTATTGCCTACGGCAGCCGCTGGATT 3' | (SEQ ID NO: 12) |
| 3) | 5' GTTATTACTCGCTGCCCAACCAGCCATGGCC 3' | (SEQ ID NO: 13) |
| 4) | 5' GAGCTCGTCAGTTCTAGAGTTAAGCGGCCG 3' | (SEQ ID NO: 14) |
| 5) | 5' CTATTTCATTATGACTGTCTCCTTGGCGACTAGTTTAGAATTCAAGCT 3' | (SEQ ID NO: 15) |
| 6) | 5' CAGCGAGTAATAACAATCCAGCGGCTGCCGTAGGCAATAG 3' | (SEQ ID NO: 16) |
| 7) | 5' TGACGAGCTCGGCCATGGCTGGTTGGG 3' | (SEQ ID NO: 17) |
| 8) | 5' TCGACGGCCGCTTAACTCTAGAAC 3' | (SEQ ID NO: 18) |

The completed synthetic DNA insert was ligated directly into the Lambda Zap™ II vector described in Example 1(a)(i) that had been previously digested with the restriction enzymes Sac I and Xho I. The ligation mixture was packaged according to the manufacture's instructions using Gigapack II Gold packing extract (Stratagene). The packaged ligation mixture was plated on XL1-Blue cells (Stratagene).

Individual Lambda plaques were cored and the inserts excised according to the in vivo excision protocol for Lambda Zap™ II provided by the manufacturer (Stratagene). This in vivo excision protocol moved the cloned insert from the Lambda Lc2 vector into a plasmid phagemid vector allow for easy manipulation and sequencing. The accuracy of the above cloning steps was confirmed by sequencing the insert using the manufacture's instructions in the AMV Reverse Transcriptase $^{35}$S-dATP sequencing kit (Stratagene).

A preferred vector for use in this invention, designated Lambda Lc3, is a derivative of Lambda Lc2 prepared above. Lambda Lc2 contains a Spe I restriction site (ACTAGT) located 3' to the EcoR I restriction site and 5' to the Shine-Dalgarno ribosome binding site. A Spe I restriction site is also present in Lambda Hc2. A combinatorial vector, designated pComb, was constructed by combining portions of Lambda Hc2 and Lc2 together as described in Example 1a(iv) below. The resultant combinatorial pComb vector contained two Spe I restriction sites, one provided by Lambda Hc2 and one provided by Lambda Lc2, with an EcoR I site in between. Despite the presence of two Spe I restriction sites, DNA homologs having Spe I and EcoR I cohesive termini were successfully directionally ligated into protocol described above. Double stranded DNA was prepared from the phagemid-containing cells according to the methods described by Holmes, et al. (*Anal. Biochem.*, 114:193, 1981). The phagemids resulting from in vivo excision contained the same nucleotide sequences for antibody fragment cloning and expression as did the parent vectors, and are designated phagemid Hc2 and Lc2, corresponding to Lambda Hc2 and Lc2, respectively.

For the construction of combinatorial phagemid vector pComb, produced by combining portions of phagemid Hc2 and phagemid Lc2, phagemid Hc2 was first digested with Sac I to remove the restriction site located 5' to the LacZ promoter. The linearized phagemid was then blunt ended with T4 polymerase and ligated to result in a Hc2 phagemid lacking a Sac I site. The modified Hc2 phagemid and the Lc2 phagemid were then separately restriction digested with Sca I and EcoR I to result in a Hc2 fragment having from 5' to 3' Sca I, not I Xho I, Spe I and EcoR I restriction sites and a Lc2 fragment having from 5' to 3' EcoR I, Sac I, Xba I and Sac I restriction sites. The linearized phagemids were then ligated together at their respective cohesive ends to form pComb, a circularized phagemid having a linear arrangement of restriction sites of Not I, Xho I, Spe I, EcoR I, Sac I, Xba I, Apa I and Sca I. The ligated phagemid vector was then inserted into an appropriate bacterial host and transformants were selected on the antibiotic ampicillin.

Selected ampicillin resistant transformants were screened for the presence of two Not I sites. The resulting ampicillin resistant combinatorial phagemid vector was designated pComb. The resultant combinatorial vector, pComb, consisted of a DNA molecule having two cassettes to express two fusion proteins and having nucleotide residue sequences for the following operatively linked elements listed in a 5' to 3' direction: a first cassette consisting of an inducible LacZ promoter upstream from the LacZ gene; a Not I restriction site; a ribosome binding site; a pelB leader; a spacer; a cloning region bordered by a 5' Xho and 3' Spe I restriction site; a decapeptide tag followed by expression control stop sequences; an EcoR I restriction site located 5' to a second cassette consisting of an expression control ribosome binding site; a pelB leader; a spacer region; a cloning region bordered by a 5'Sac I and a 3' Xba I restriction site followed by expression control stop sequences and a second Not I restriction site.

A preferred combinatorial vector designated pComb3, is constructed by combining portions of phagemid Hc2 and phagemid Lc3 as described above for preparing pComb. The resultant combinatorial vector, pComb3, consists of a DNA molecule having two cassettes identical to pComb to express two fusion proteins identically to pComb except that a second Spe I restriction site in the second cassette is eliminated.

b. Construction of Vector pCombIII for Expressing Fusion Proteins having a Bacteriophage Coat Protein Membrane Anchor Because of the multiple endonuclease restriction cloning sites, the pComb phagemid expression vector prepared above is a useful cloning vehicle for modification for the preparation of an expression vector of this invention. To that end, pComb is digested with EcoR I and Spe I followed by phosphatase treatment to produce linearized pComb.

(ii) Preparation of pCombIII

A separate phagemid expression vector was constructed using sequences encoding bacteriophage cpIII membrane anchor domain. A PCR product defining the DNA sequence encoding the filamentous phage coat protein, cpIII, membrane anchor containing a LacZ promotor region sequence 3' to the membrane anchor for expression of the light chain and Spe I and EcoR I cohesive termini was prepared from M13mp18, a commercially available bacteriophage vector (Pharmacia, Piscataway, N.J.).

To prepare a modified cpIII, replicative form DNA from M13mp18 was first isolated. Briefly, into 2 ml of LB (Luria-Bertani medium), 50 µl of a culture of a bacterial strain carrying an F' episome (JM107, JM109 or TG1) were admixed with a one tenth suspension of bacteriophage particles derived from a single plaque. The admixture was incubated for 4 to 5 hours at 37° C. with constant agitation. The admixture was then centrifuged at 12,000×g for 5 minutes to pellet the infected bacteria. After the supernatant was removed, the pellet was resuspended by vigorous vortexing in 100 µl of ice-cold solution I. Solution I was prepared by admixing 50 mM glucose, 10 mM EDTA (disodium ethylenediaminetetraacetic acid) and 25 mM Tris-HCl at pH 8.0, and autoclaving for 15 minutes.

To the bacterial suspension, 200 µl of freshly prepared Solution II was admixed and the tube was rapidly inverted five times. Solution II was prepared by admixing 0.2 N NaOH and 1% SDS. To the bacterial suspension, 150 µl of ice-cold Solution III was admixed and the tube was vortexed gently in an inverted position for 10 seconds to disperse Solution III through the viscous bacterial lysate. Solution III was prepared by admixing 60 ml of 5 M potassium acetate, 11.5 ml of glacial acetic acid and 28.5 ml of water. The resultant bacterial lysate was then stored on ice for 5 minutes followed by centrifugation at 12,000×g for 5 minutes at 4° C. in a microfuge. The resultant supernatant was recovered and transferred to a new tube. To the supernatant was added an equal volume of phenol/chloroform and the admixture was vortexed. The admixture was then centrifuged at 12,000×g for 2 minutes in a microfuge. The resultant supernatant was transferred to a new tube and the double-stranded bacteriophage DNA was precipitated with 2 volumes of ethanol at room temperature. After allowing the admixture to stand at room temperature for 2 minutes, the admixture was centrifuged to pellet the DNA. The supernatant was removed and the pelleted replicative form DNA was resuspended in 25 µl of Tris-HCl at pH 7.6, and 10 mM EDTA (TE).

The double-stranded M13mp18 replicative form DNA was then used as a template for isolating the gene encoding the membrane anchor domain at cpIII. M13mp18 replicative form DNA was prepared as described above and used as a template for two PCR amplifications for construction of a DNA fragment consisting of the mature gene for cpIII membrane anchor domain located 5' to a sequence encoding the LacZ promoter, operator and cap-binding site for controlling light chain expression. The restriction sites, Spe I and EcoR I, were created in the amplification reactions and were located at the 5' and 3' ends of the fragment respectively. The procedure for creating this fragment by combining the products of two separate PCR amplifications is described below.

The primer pair, G-3(F) (SEQ ID NO: 19) and G-3(B) (SEQ ID NO: 20) listed in Table 3, was used in the first PCR reaction as performed above to amplify the cpIII membrane anchor gene and incorporate Spe I and Nhe I restriction sites into the fragment. For the PCR reaction, 2 µl containing 1 ng of M13mp18 replicative form DNA were admixed with 10 µl of 10× PCR buffer purchased commercially (Promega Biotech, Madison, Wis.) in a 0.5 ml microfuge tube. To the DNA admixture, 8 µl of a 2.5 mM solution of dNTPs (dATP, dCTP, dGTP, dTTP) were admixed to result in a final concentration of 200 micromolar (µM). Three µl (equivalent to 60 picomoles (pM)) of the G-3(F) primer and 3 µl (60 pM) of the 3' backward G-3(B) primer were admixed into the DNA solution. To the admixture, 73 µl of sterile water and 1 µl/5 units of polymerase (Promega Biotech) were added. Two drops of mineral oil were placed on top of the admixture and 40 rounds of PCR amplification in a thermocycler were performed. The amplification cycle consisted of 52° C. for 2 minutes, 72° C. for 1.5 minutes and 91° C. for 2 minutes. The resultant PCR modified cpIII membrane anchor domain DNA fragment from M13mp18 containing samples were then purified with Gene Clean (BIO101, La Jolla, Calif.), extracted twice with phenol/chloroform, once with chloroform followed by ethanol precipitation and were stored at −70° C. in 10 mM Tris-HCl at pH 7.5, and 1 mM EDTA.

The resultant PCR modified cpIII DNA fragment having Spe I and Nhe I sites in the 5' and 3' ends, respectively, of the fragment was verified by electrophoresis in a 1% agarose gel. The area in the agarose containing the modified cpIII DNA fragment was isolated from the agarose. The resultant amplified PCR fragment also contained nucleotide sequences for encoding a five amino acid tether composed of four glycine residues and one serine juxtaposed between the heavy chain and cpIII encoding domains. Once expressed, the five amino acid residue sequence lacking an orderly secondary structure served to minimize the interaction between the Fab and cpIII domains.

A second PCR amplification using the primer pairs, Lac-F (SEQ ID NO: 21) and Lac-B (SEQ ID NO: 22) listed in Table 3, was performed on a separate aliquot of M13mp18 replicative form template DNA to amplify the LacZ promoter, operator and Cap-binding site having a 5' Nhe I site and a 3' EcoR I site. The primers used for this amplification were designed to incorporate a Nhe I site on the 5' end of the amplified fragment to overlap with a portion of the 3' end of the cpIII gene fragment and of the Nhe I site 3' to the amplified cpIII fragment. The reaction and purification of the PCR product was performed as described above.

An alternative Lac-B primer for use in constructing the cpIII membrane anchor and LacZ promotor region was Lac-B' as shown in Table 3. The amplification reactions were performed as described above with the exception that in the second PCR amplification, Lac-B' was used with Lac-F instead of Lac-B. The use of Lac-B' resulted in a LacZ region lacking 29 nucleotides on the 3' end but was functionally equivalent to the longer fragment produced with the Lac-F and Lac-B primers.

The products of the first and second PCR amplifications using the primer pairs G-3(F) and G-3(B) and Lac-F and Lac-B were then recombined at the nucleotides corresponding to cpIII membrane anchor overlap and Nhe I restriction site and subjected to a second round of PCR using the G-3(F) (SEQ ID NO: 19) and Lac-B (SEQ ID NO: 22) primer pair to form a recombined PCR DNA fragment product consisting of the following: a 5' Spe I restriction site; a cpIII DNA membrane anchor domain beginning at the nucleotide residue sequence which corresponds to the amino acid residue 198 of the entire mature cpIII protein; an endogenous stop site provided by the membrane anchor at amino acid residue number 112; a Nhe I restriction site, a LacZ promoter, operator and Cap-binding site sequence; and a 3' EcoR I restriction site.

To construct a phagemid vector for the coordinate expression of a heavy chain-cpIII fusion protein with kappa light chain, the recombined PCR modified cpIII membrane anchor domain DNA fragment was then restriction digested with Spe I and EcoR I to produce a DNA fragment for directional ligation into a similarly digested pComb2 phagemid expression vector having only one Spe I site prepared in Example 1a4) to form a pComb2-III (also referred to as pComb2-III) phagemid expression vector. Thus, the resultant ampicillin resistance conferring pComb2-3 vector, having only one Spe I restriction site, contained separate LacZ promoter/operator sequences for directing the separate expression of the heavy chain (Fd)-cpIII fusion product and the light chain protein. The expressed proteins were directed to the periplasmic space by pelB leader sequences for functional assembly on the membrane. Inclusion of the phage F1 intergenic region in the vector allowed for packaging of single stranded phagemid with the aid of helper phage. The use of helper phage superinfection lead to expression of two forms of cpIII. Thus, normal phage morphogenesis was perturbed by competition between the Fab-cpIII fusion and the native cpIII of the helper phage for incorporation into the virion for Fab-cpVIII fusions. In addition, also contemplated for use in this invention are vectors conferring chloramphenicol resistance and the like.

A more preferred phagemid expression vector for use in this invention having additional restriction enzyme cloning sites, designated pComb-III' or pComb2-3', was prepared as described above for pComb2-3 with the addition of a 51 base pair fragment from pBluescript as described by Short, et al., *Nuc. Acids Res.*, 16:7583–7600 (1988) and commercially available from Stratagene. To prepare pComb2-3', pComb2-3 was first digested with Xho I and Spe I restriction enzymes to form a linearized pComb2-3. The vector pBluescript was digested with the same enzymes releasing a 51 base pair fragment containing the restriction enzyme sites Sal I, Acc I, Hinc II, Cla I, Hind III, EcoR V, Pst I, Sma I and BamH I. The 51 base pair fragment was ligated into the linearized pComb2-3 vector via the cohesive Xho I and Spe I termini to form pComb2-3'.

TABLE 3

| SEQ ID NO: | Primer | |
|---|---|---|
| 19[1] | G-3 (F) | 5' GAGACG<u>ACTAGT</u><u><u>GGTGGCGGTGGCTCTCCATTCGTTTGTGAATATCAA</u></u> 3' |
| 20[2] | G-3 (B) | 5' TTACTA<u>GCTAGC</u><u><u>ATAATAACGGAATACCCAAAAGAACTGG</u></u> 3' |
| 21[3] | LAC-F | 5' <u>TATGCTAGCTAGTAA</u>CACGACAGGTTTCCCGACTGG 3' |
| 22[4] | LAC-B | 5' ACCGAGCTC<u>GAATTC</u>GTAATCATGGTC 3' |
| 23[5] | LAC-B' | 5' AGCTGTT<u>GAATTC</u>GTGAAATTGTTATCCGCT 3' |

F Forward Primer
B Backward Primer
[1]From 5' to 3': Spe I restriction site sequence is single under-lined; the overlapping sequence with the 5' end of cpIII is double underlined
[2]From 5' to 3': Nhe I restriction site sequence is single under-lined; the overlapping sequence with 3' end of cpIII is double underlined.
[3]From 5' to 3': overlapping sequence with the 3' end of cpIII is double underlined; Nhe I restriction sequence begins with the nucleotide residue "G" at position 4 and extends 5 more residues = GCTAGC.
[4]EcoR I restriction site sequence is single underlined.
[5]Alternative backwards primer for amplifying LacZ; EcoR I restriction site sequence is single underlined.

EXAMPLE 2

Isolation of Human HSV-specific Monoclonal Antibodies Produced from the Dicistronic Expression Vector, pComb2-3

In practicing this invention, the heavy (Fd consisting of $V_H$ and $C_H1$) and light (kappa) chains ($V_L$, $C_L$) of antibodies are first targeted to the periplasm of *E. coli* for the assembly of heterodimeric Fab molecules. In order to obtain expression of antibody Fab libraries on a phage surface, the nucleotide residue sequences encoding either the Fd or light chains must be operatively linked to the nucleotide residue sequence encoding a filamentous bacteriophage coat protein membrane anchor. A coat protein for use in this invention in providing a membrane anchor is III (cpIII or cp3). In the Examples described herein, methods for operatively linking a nucleotide residue sequence encoding a Fd chain to a cpIII membrane anchor in a fusion protein of this invention are described.

In a phagemid vector, a first and second cistron consisting of translatable DNA sequences are operatively linked to form a dicistronic DNA molecule. Each cistron in the dicistronic DNA molecule is linked to DNA expression control sequences for the coordinate expression of a fusion protein, Fd-cpIII, and a kappa light chain.

The first cistron encodes a periplasmic secretion signal (pelB leader) operatively linked to the fusion protein, Fd-cpIII. The second cistron encodes a second pelB leader operatively linked to a kappa light chain. The presence of the pelB leader facilitates the coordinated but separate secretion of both the fusion protein and light chain from the bacterial cytoplasm into the periplasmic space.

In this process, the phagemid expression vector carries an ampicillin selectable resistance marker gene (beta lactamase or bla) in addition to the Fd-cpIII fusion and the kappa chain. The f1 phage origin of replication facilitates the generation of single stranded phagemid. The isopropyl thiogalactopyranoside (IPTG) induced expression of a dicistronic message encoding the Fd-cpIII fusion ($V_H$, $CH_{H1}$, cpIII) and the light chain ($V_L$, $C_L$) leads to the formation of heavy and light chains. Each chain is delivered to the periplasmic space by the pelB leader sequence, which is subsequently cleaved. The heavy chain is anchored in the membrane by the cpIII membrane anchor domain while the light chain is secreted into the periplasm. The heavy chain in the presence of light chain assembles to form Fab molecules. This same result can be achieved if, in the alternative, the light chain is anchored in the membrane via a light chain fusion protein having a membrane anchor and heavy chain is secreted via a pelB leader into the periplasm.

With subsequent infection of *E. coli* with a helper phage, as the assembly of the filamentous bacteriophage progresses, the coat protein III is incorporated on the tail of the bacteriophage.

a. Preparation of Lymphocyte RNA

Five milliliters of bone marrow was removed by aspiration from a HIV-1 seropositive individual exhibiting a high titer (greater than 1:80) of antibodies to Herpes simplex virus (hereinafter referred to as HSV). Total cellular RNA was prepared from the bone marrow lymphocytes as described above using the RNA preparation methods described by Chomczynski, et al., *Anal Biochem.*, 162:156–159 (1987) and using the RNA isolation kit (Stratagene) according to the manufacturer's instructions. Briefly, for immediate homogenization of the cells in the isolated bone marrow, 10 ml of a denaturing solution containing 3.0 M guanidinium isothiocyanate containing 71 $\mu$l of beta-mercaptoethanol were admixed to the isolated bone marrow. One ml of sodium acetate at a concentration of 2 M at pH 4.0 was then admixed with the homogenized cells. One ml of phenol that had been previously saturated with $H_2O$ was also admixed to the denaturing solution containing the homogenized spleen. Two ml of a chloroform:isoamyl alcohol (24:1 v/v) mixture was added to this homogenate. The homogenate were mixed vigorously for ten seconds and maintained on ice for 15 minutes. The homogenate was then transferred to a thick-walled 50 ml polypropylene centrifuged tube (Fisher Scientific Company, Pittsburgh, Pa.). The solution was centrifuged at 10,000×g for 20 minutes at 4° C. The upper RNA-containing aqueous layer was transferred to a fresh 50 ml polypropylene centrifuge tube and mixed with an equal volume of isopropyl alcohol. This solution was maintained at −20° C. for at least one hour to precipitate the RNA. The solution containing the precipitated RNA was centrifuged at 10,000×g for twenty minutes at 4° C. The pelleted total cellular RNA was collected and dissolved in 3 ml of the denaturing solution described above. Three ml of isopropyl alcohol were added to the re-suspended total cellular RNA and vigorously mixed. This solution was maintained at −20° C. for at least 1 hour to precipitate the RNA. The solution containing the precipitated RNA was centrifuged at 10,000×g for ten minutes at 4° C. The pelleted RNA was washed once with a solution containing 75% ethanol. The pelleted RNA was dried under vacuum for 15 minutes and then re-suspended in dimethyl pyrocarbonate-treated (DEPC-$H_2O$) $H_2O$.

Messenger RNA (mRNA) enriched for sequences containing long poly A tracts was prepared from the total cellular RNA using methods described in *Molecular Cloning: A Laboratory Manual*, Maniatis, et al., eds., Cold Spring Harbor, N.Y. (1982). Briefly, one half of the total RNA isolated from a single donor prepared as described above was resuspended in one ml of DEPC-$H_2O$ and maintained at 65° C. for five minutes. One ml of 2× high salt loading buffer consisting of 100 mM Tris-HCl, 1 M NaCl, 2.0 mM EDTA at pH 7.5, and 0.2% SDS was admixed to the resuspended RNA and the mixture allowed to cool to room temperature.

The total purified mRNA was then used in PCR amplification reactions as described in Example 2b. Alternatively, the mRNA was further purified to poly A+ RNA by the following procedure. The total MRNA was applied to an oligo-dT (Collaborative Research Type 2 or Type 3) column that was previously prepared by washing the oligo-dT with a solution containing 0.1 M sodium hydroxide and 5 mM EDTA and then equilibrating the column with DEPC-$H_2O$. The eluate was collected in a sterile polypropylene tube and reapplied to the same column after heating the eluate for 5 minutes at 65° C. The oligo-dT column was then washed with 2 ml of high salt loading buffer consisting of 50 mM Tris-HCl at pH 7.5, 500 mM sodium chloride, 1 mM EDTA at pH 7.5 and 0.1% SDS. The oligo dT column was then washed with 2 ml of 1× medium salt buffer consisting of 50 mM Tris-HCl at pH 7.5, 100 mM, 1 mM EDTA and 0.1% SDS. The messenger RNA was eluted from the oligo-dT column with 1 ml of buffer consisting of 10 mM Tris-HCl at pH 7.5, 1 mM EDTA at pH 7.5, and 0.05% SDS. The messenger RNA was purified by extracting this solution with phenol/chloroform followed by a single extraction with 100% chloroform. The messenger RNA was concentrated by ethanol precipitation and resuspended in DEPC $H_2O$. The resultant purified mRNA contained a plurality of anti-herpes simplex virus (HSV) antibodies encoding $V_H$ and $V_L$ sequences for preparation of an anti-HSV Fab DNA library.

EXAMPLE 3 a. Library Construction, Screening and Fab Production

The preparation of human antibody Fab libraries displayed on the surface of M13 phage has been described above. The library was constructed as an IgG1κFab library using bone marrow lymphocyte RNA of a long term asymptomatic HIV-1 positive individual. Antigen binding phage were selected against HSV-1 and -2 viral lysates (monkey kidney epithelial cells (VERO), 36 hr post infection, were pelleted and lysed using phosphate-buffered saline containing 1% sodium deoxycholate, 1% NP 40 (SIGMA), 0.1 mM DIFP and 2 mg/ml aprotinin) bound to ELISA wells (Sigma) through a panning procedure described in Burton, et al., *Proc. Nat'l. Acad. Sci.* USA, 88:10134–10137, 1991;

Barbas, et al., *Methods*, 2:119–124, 1991. Phage from the final round of panning were converted to a soluble Fab expressing phagemid system and these clones selected for reactivity in ELISA with the antigen against which they were panned. Specific antibody was affinity purified from bacterial supernates over a protein A/G matrix (Shleicher & Schuell) as described in Williamson, et al., *Proc. Nat'l. Acad. Sci.* USA, 90:4141–4145, 1993.

b. Viruses and Cells

Vero cells were grown in RPMO 1640 supplemented with 5% fetal calf serum (FCS). HSV-1 and HSV-2 (strain F and G, respectively, ATCC, Rockville, Md.) were infected into Vero cells and virus titers were determined by plaque-assay and expressed as pfu ml$^{-1}$.

c. Neutralization Activity

Crude *E.coli* extracts, positive in an ELISA screen using the same antigen preparation against which the library was panned, were tested for their ability to neutralize HSV-1 or HSV-2 at 1:5–1:10 dilutions according to the procedure described below. The Fabs that displayed neutralizing activity were affinity purified and their neutralizing titers were determined as follows. About 250 pfu of HSV-1 or HSV-2 were incubated with serial dilutions of recombinant Fabs for 1 hr at 37° C. and then adsorbed for 1 hr at 37° C. on Vero cell monolayers grown in six well plates. After adsorption, the inoculum was removed and the cells washed and overlaid with MEM containing 0.5% agarose and 2% FCS. After 72 hrs, the plates were fixed with 10% formaldehyde in phosphate-buffered saline (PBS) for 30 min, the nutrient agar overlay was removed and the cells were strained with a 1% solution of crystal violet in 70% methanol for 30 min. The stained monolayers were then washed and the plaques were counted.

d. Inhibition of Plague Development Assay

Monolayers of Vero cells were infected with of 50–100 pfu of HSV-1 for 3 hrs at 37° C. They were then washed and the medium replaced with nutrient agar containing 25, 5 or 1 μg/ml of recombinant Fab. After 72 hrs or 86 hrs, they were fixed and stained as described above. Plaque diameter was measured with a digital caliper (Mitutoyo, Japan). At least 10 plaques were measured per well. Plaques below 0.2 mm in diameter were considered abortive and therefore not counted. Statistical calculations were performed by analysis of variants (Sheffe F-test).

e. Post-attachment Neutralization Assay

About 250 pfu of HSV-1 were adsorbed at 4° C. for 90 min on Vero monolayers prechilled at 4° C. for 15 min. The inoculum was then removed and the cells washed and overlaid with medium containing serial dilutions of recombinant Fab (5, 1, 0.2, 0.04 μg/ml) at 4° C. to prevent penetration of virus. After 90 min the Fab-containing medium was removed and after washing, replaced with nutrient agar. For the purpose of control, equal amounts of virus were preincubated at 4° C. with serial dilutions (5, 1, 0.2, 0.04 μg/ml) of the same Fab (pre-attachment neutralization). After 90 min these virus/antibody dilutions were adsorbed onto Vero monolayers (prechilled at 4° C. for 1 hr and 45 min) for 90 min. The inoculum was then removed and the cells washed and overlaid with nutrient agar. After 72 hr, the monolayers were fixed and strained as described above for the neutralization assays.

f. Nucleic Acid Sequencing

Nucleic acid sequencing was performed with a 373A automated DNA sequencer (Applied Biosystems) using a Taq fluorescent dideoxy-nucleotide terminator cycle sequencing kit (Applied Biosystems). Primers used for the elucidation of light and heavy chain sequence have been previously described in Williamson, et al., (*Proc. Nat'l Acad. Sci.* USA, 90:4141–4145, 1993).

g. Identification of Antibody Binding Protein by Immunoprecipitation

HSV-2 infected cells were harvested and sonicated in PBS containing 1% sodium deoxycholate, 1% NP40 (Sigma), 0.1 mM di-isopropyl-fluorophosphate fluorophosphate (DIFP) and 2 mg/ml aprotinin. Lysates (50 μl) were then incubated with 7.5 μg of recombinant Fab for 1 hour at 4° C. Immune complexes were precipitated with an agarose-bound goat anti-human (20 μl) resolved on a 10% SDS-PAGE and electro-blotted onto nylon membranes (BioRad) in 1× Towbin buffer. Western blots were performed according to standard protocols. Briefly, blots were blocked with 5% non-fat dry milk in Tris-buffered saline (TBS) and probed with a panel of established mouse monoclonal anti-HSV antibodies (Goodwin Institute) in 1% non-fat dry milk in TBS containing 0.05% Tween 20. Detection was performed with a goat anti-mouse antibody conjugated to alkaline phosphatase and chemiluminescence (BioRad). Blots were also immunoreacted with a rabbit polyclonal anti-HSV for the purpose of control and detected with a goat anti-rabbit antibody conjugated to alkaline phosphatase (BioRad).

h. Purification of Fabs

One liter cultures of super broth containing 50 μg/ml carbenicillin and 20 mM MgCl$_2$ were inoculated with appropriate clones and induced 7 hours later with 2 mM IPTG and grown overnight at 30° C. The cell pellets were sonicated and the supernatant concentrated to 50 ml. The filtered supernatants were loaded on a 25 ml protein G-anti-Fab column, washed with 12 ml buffer at 3 ml/min., and eluted with citric acid, pH 2.3. The neutralized fractions were then concentrated and exchanged into 50 mM MES pH 6.0 and loaded onto a 2 ml Mono-S column at 1 ml/min. A gradient of 0–500 mM NaCl was run at 1 ml/min with the Fab eluting in the range of 200–250 mM NaCl. After concentration, the Fabs were positive when titered by ELISA against FG and gave a single band at 50 kD by 10–15% SDS-PAGE. Concentration was determined by absorbance measurement at 280 nm using an extinction coefficient (1 mg/ml) of 1.35.

EXAMPLE 4

Neutralizing Activity of Fab Against HSV

A large panel of human combinatorial antibody Fab fragments specific for HSV-1 and -2 were isolated as described in Example 2. These antibodies were generated by independently panning an IgG1k Fab library of 2×10$^6$ members against whole lysate of these two viruses.

Enrichment of antigen specific phage, as determined by the number of phage eluted from HSV coated ELISA wells, was measured through 4 rounds of library panning. A 25-fold amplification was seen in the case of the panning with HSV-2 viral lysate, while a 20-fold amplification was observed using the HSV-1 viral lysate.

Soluble Fabs were then produced as described in Barbas, et al., *Proc. Nat'l Acad. Sci.* USA 88:7978–7982, 1991. Briefly, the phage coat protein III was excised from the phage display vector and the DNA self-ligated to give a vector producing soluble Fabs. Subsequently protein synthesis was induced overnight using IPTG and the bacterial pellet sonicated to release Fab from the periplasmic space. The Fab supernates were then tested, both in ELISA against the antigen with which they were panned and in immunofluorescence studies with virus-infected cells. Ten out of twenty clones taken from the final round of panning with HSV-1 viral lysate were positive in both assays, while 15 out of twenty were positive in the panning against HSV-2 lysate. All clones demonstrating positive reactivity with one virus type were further shown to be cross-reactive with the other in both immunofluorescence and ELISA assays. This probably reflects the known similarity between many of the proteins of HSV-1 and -2.

DNA sequences were determined as described above and the deduced amino acid sequences of the heavy chain variable domains were determined for several of the virus-specific clones. Nine of 18 of the heavy chain sequences obtained from the HSV-2 panning were all quite different from each other. Similarly, 5 of 8 heavy chains taken from the HSV-1 panning were largely unrelated. A comparison of the targets to which these different antibodies are directed with the serum antibody reactivity of the donor indicates how accurately the library approach represents the humoral response of the donor to virus.

Although virus type cross-reactivity in ELISA was exhibited by all of the Fabs described here, only one heavy chain sequence was common to both pannings. Thus, despite the reported similarity between virions of HSV-1 and HSV-2 and the observed binding properties of the isolated Fabs, each virus selected distinct antibody molecules from the library. This implies differences between HSV-1 and -2 either in the antigens presented to the library or in the antibody response to the two viruses.

Neutralizing activity for all positive clones was estimated in plaque reduction and inhibition of plaque development assays of HSV-1 and -2, as described above. Three of the Fabs obtained from the HSV-2 panning exhibited a marked neutralization activity in both assays and with both virus types when tested as crude bacterial supernatants in vitro. These clones were shown to have identical heavy and light chain sequences. Accordingly, one of these Fab clones (Fab8), was grown in quantity, affinity purified and further characterized.

Figure 2A:
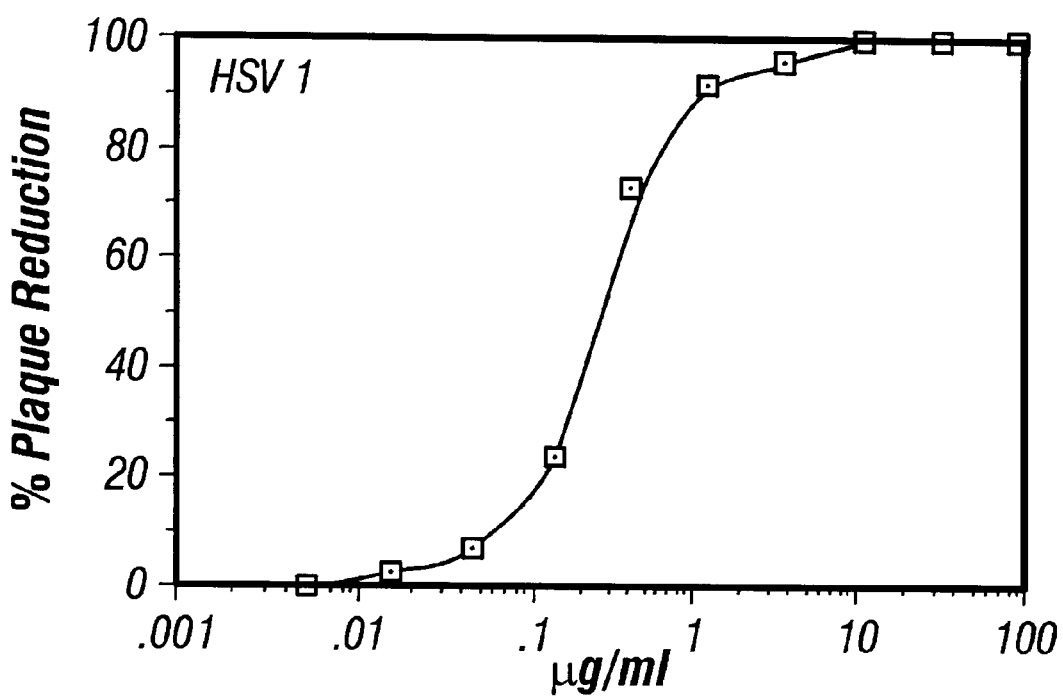
FIG. 2A shows activity against HSV-1 and FIG. 2B shows activity against HSV-2. Purified Fab8 neutralized HSV-1 with a 50% inhibition at about 0.25 $\mu$g/ml and with an 80% inhibition at 0.6 $\mu$g/ml, while HSV-2 was neutralized with a 50% inhibition at about 0.05 $\mu$g/ml and an 80% inhibition at 0.1 $\mu$g/ml.
Figure 2B:
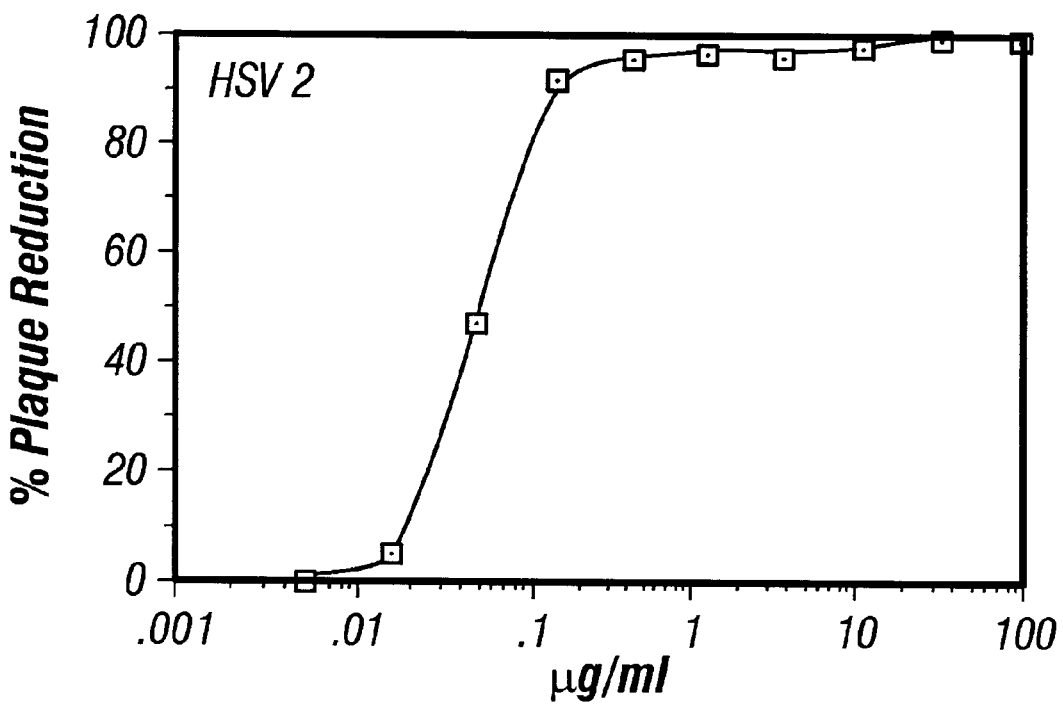
Figure 3A:
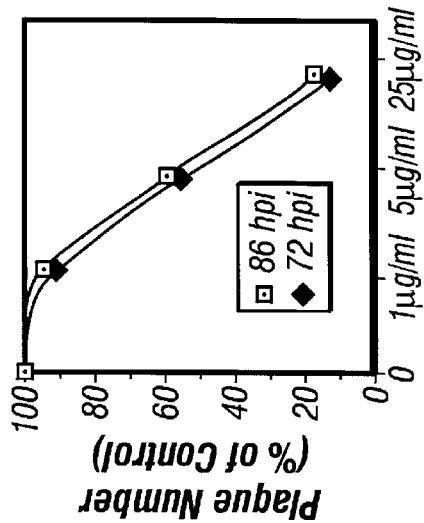
FIG. 3A shows statistically significant reduction in plaque size was observed at concentrations of 5 and 1 $\mu$g/ml (*=p>0.01), with an approximate 50% reduction in plaque size at 5 $\mu$g/ml. The number of plaques was also dramatically reduced at Fab concentrations of 5 and 25 $\mu$g/ml (FIG. 3B, FIG. 3D). At 25 $\mu$g/ml and 72 hrs hpi plaque development in HSV-2 infected monolayers was completely inhibited (FIG. 3C, FIG. 3D).
Figure 3B:
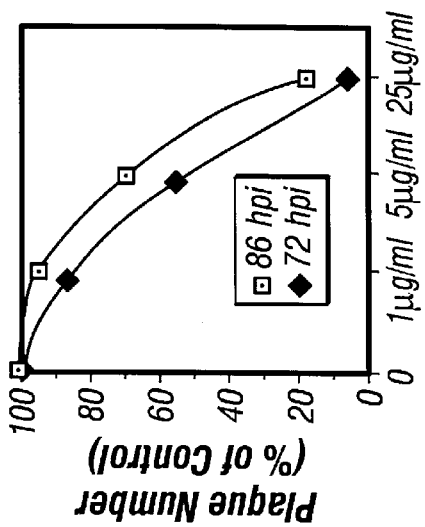
FIG. 3 shows an inhibition of plaque development assay. Purified Fab8 inhibited the development of plaques when applied 4 hours post-infection (hpi) on monolayers infected with HSV-1 (FIG. 3A, FIG. 3B) or HSV-2 (FIG. 3C, FIG. 3D) 4 hours post infection.
FIG. 3E shows an inhibition of plaque development assay with HSV-2 infected monolayers at a number of different Fab concentrations 86 hpi.
Figure 3C:
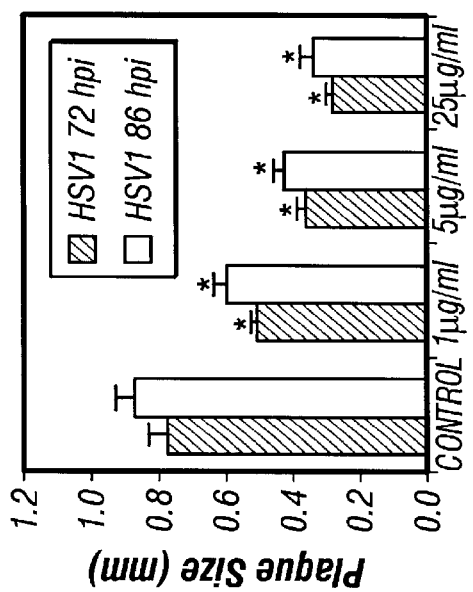
Figure 3D:
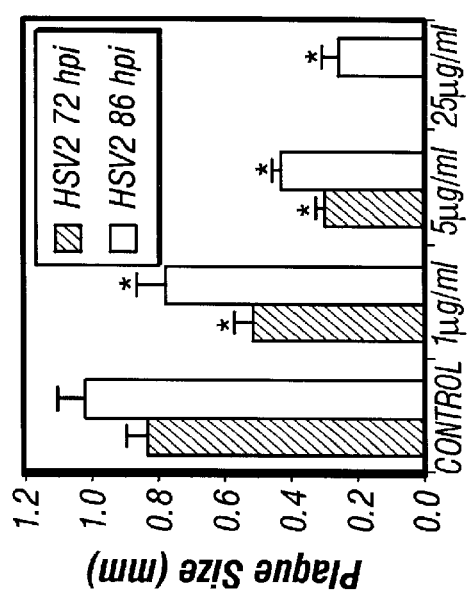
Figure 3E:
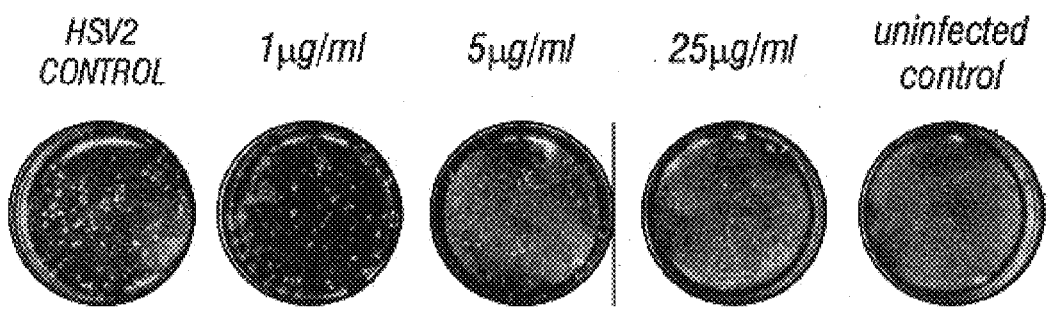

The Fab8 antibody was able to recognize both types of the virus. This antibody was shown to neutralize HSV-2 (50% inhibition at about 0.05 $\mu$g/ml) somewhat more efficiently than HSV-1 (50% inhibition at about 0.25 $\mu$g/ml and 80% inhibition at 0.6 $\mu$g/ml) (FIG. 2). FIG. 2 shows the neutralizing activity of Fab8, as measured by plaque reduction. FIG. 2A shows activity against HSV-1 and FIG. 2B shows activity against HSV-2. Purified Fab8 neutralized HSV-1 with a 50% inhibition at about 0.25 $\mu$g/ml and with an 80% inhibition at 0.6 $\mu$g/ml, while HSV-2 was neutralized with a 50% inhibition at about 0.05 $\mu$g/ml and an 80% inhibition at 0.1 $\mu$g/ml.

These figures suggest that Fab8 is approximately an order of magnitude more potent than most murine neutralizing antibodies described so far (Navarro, et al., *Virology*, 186:99–112, 1992; Fuller, et al., *J. Virol*, 55:475–482, 1985), although recently reported anti-gB and anti-gD humanized murine antibodies may be equally potent (Deschamps, et al., *Proc. Nat'l Acad. Sci.* USA, 88:2869–2873, 1991). However, the mouse and humanized antibodies are bivalent whole IgG molecules rather than human derived Fab fragments. Also, eukaryotic expression of the recombinant Fab of the invention as an intact IgG molecule may significantly enhance its virus neutralization potency.

The Fab8 antibody also inhibited plaque formation when applied to virus-infected monolayers (FIG. 3). FIG. 3 shows an inhibition of plaque development assay. Purified Fab8 inhibited the development of plaques when applied 4 hours post-infection (hpi) on monolayers infected with HSV-1 (FIG. 3A, FIG. 3B) or HSV-2 (FIG. 3C, FIG. 3D) 4 hours post infection. FIG. 3A shows statistically significant reduction in plaque size was observed at concentrations of 5 and 1 $\mu$g/ml (*=p<0.01), with an approximate 50% reduction in plaque size at 5 $\mu$g/ml. The number of plaques was also dramatically reduced at Fab concentrations of 5 and 25 $\mu$l/ml (FIG. 3B, FIG. 3D). At 25 $\mu$g/ml and 72 hrs hpi plaque development in HSV-2 infected monolayers was completely inhibited (FIG. 3C, FIG. 3D). FIG. 3E shows an inhibition of plaque development assay with HSV-2 infected monolayers at a number of different Fab concentrations 86 hpi.

At a concentration of 25 $\mu$g/ml Fab8 completely abolished HSV-2 plaque development at 72 hrs post-infection, while a statistically significant reduction in plaque size (>50%) was observed at concentrations of 5 $\mu$g/ml and 1 $\mu$g/ml for both HSV-1 and HSV-2. Since it is accepted that plaques develop by spreading of virus to adjacent cells, the inhibition of plaque development assay determines the ability of an antibody to prevent cell-to-cell spread.

Figure 4A:
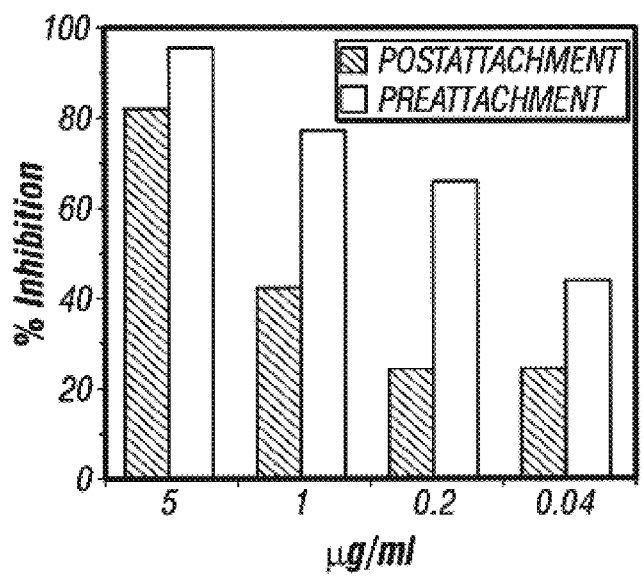
FIG. 4A shows the percentage of plaque reduction pre- and post-attachment at different Fab concentrations.
Figure 4B:
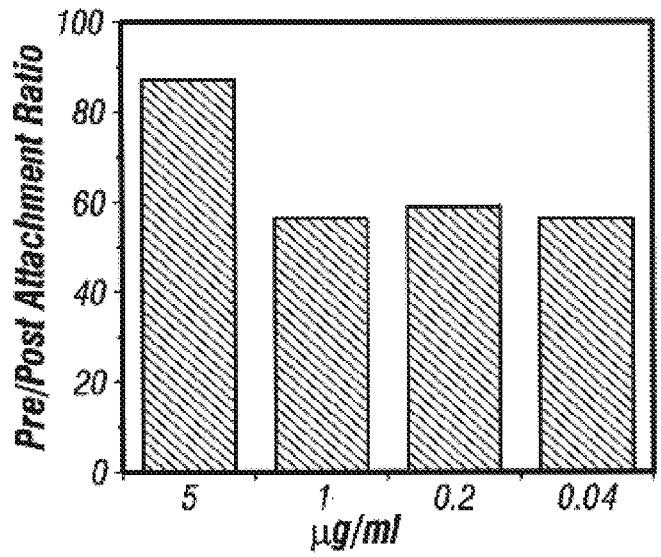
FIG. 4B shows the post-/pre-attachment neutralization ratio at different Fab concentrations.

Furthermore, this antibody strongly reduced infectivity after HSV-1 attachment (FIG. 4). FIG. 4 shows a post-attachment neutralization assay. Fab8 reduced HSV-1 infectivity after virion attachment. FIG. 4A shows the percentage of plaque reduction pre- and post-attachment at different Fab concentrations. FIG. 4B shows the post-/pre-attachment neutralization ratio at different Fab concentrations.

The pre-attachment/post attachment neutralization ratio was over 87% at an antibody concentration of 5 $\mu$g/ml, dropping to between 55–60% below 1 $\mu$g/ml. This suggests that the inhibitory action of the antibody takes place either at the level of membrane fusion, or during virus penetration or uncoating.

Figure 5:
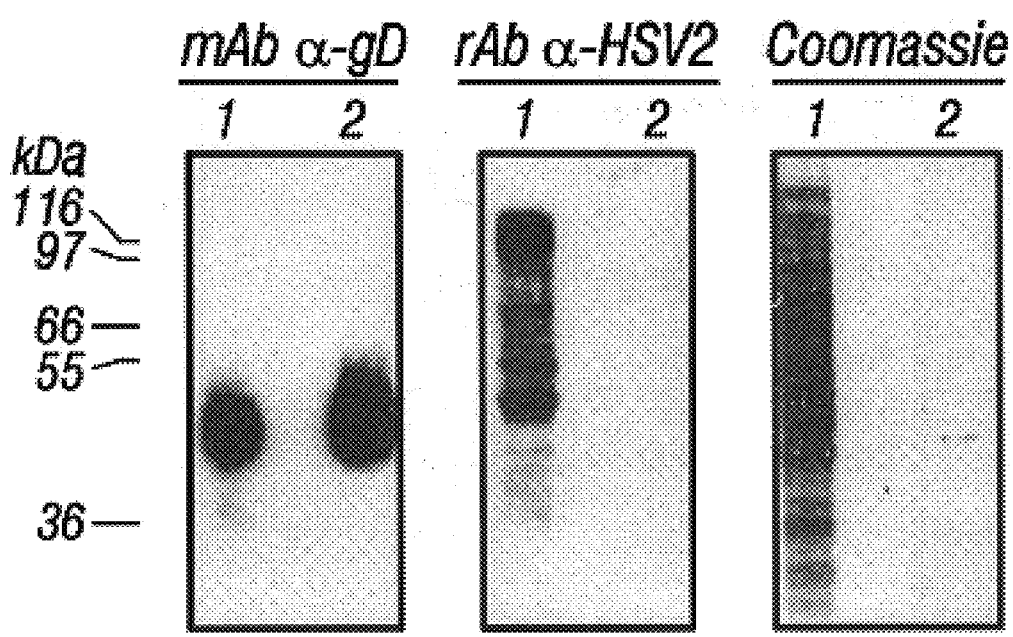
FIG. 5 shows the identification of the protein recognized by Fab8. SDS-PAGE of total proteins from HSV-2 infected Vero cells (lanes 1) and of the product of immunoprecipitation with Fab8 (lanes 2). Western blots performed in parallel were probed with a mouse monoclonal anti gD antibody (MAB $\alpha$-gD) and for the purpose of control, a rabbit polyclonal anti-HSV-2 preparation (RAB $\alpha$-HSV2). The Coomassie stain of a gel run in parallel is also shown. Fab8 immunoprecipitated a band of apparent molecular weight 48–50 kD which was recognized by a mouse monoclonal specific for gD, but not by mouse monoclonal antibodies against other HSV glycoproteins.

The protein recognized by Fab8 was identified via immunoprecipitation from whole lysate of HSV-2 infected cells. The precipitated proteins were blotted following resolution through SDS-PAGE and probed with a mouse monoclonal anti-gD and a rabbit polyclonal anti-HSV-2 (FIG. 5). FIG. 5 shows the identification of the protein recognized by Fab8. SDS-PAGE of total proteins from HSV-2 infected Vero cells (lanes 1) and of the product of immunoprecipitation with Fab8 (lanes 2). Western blots performed in parallel were probed with a mouse monoclonal anti gD antibody (MAB $\alpha$-gD) and for the purpose of control, a rabbit polyclonal anti-HSV-2 preparation (RAB $\alpha$-HSV2). The Coomassie stain of a gel run in parallel is also shown. Fab8 immunoprecipitated a band of apparent molecular weight 48–50 kD which was recognized by a mouse monoclonal specific for gD, but not by mouse monoclonal antibodies against other HSV glycoproteins.

The results illustrated in FIG. 5 show that the recombinant Fab recognizes a protein of molecular weight approximately 48–50 kD that is also reactive with murine monoclonal anti-gD. No further proteins were detected on the blot by the rabbit anti-HSV-2 polyclonal antibody preparation thus confirming the specificity of the human Fab.

Fab8 has been shown to neutralize virus extremely efficiently and to inhibit viral spread from cell to cell. The demonstration of such antiviral activity by an Fab offers potential advantages over whole IgG for some in vivo applications. Although the serum half life of Fab is dramatically shorter than that of whole IgG, the smaller molecule has far greater tissue penetration (Yokota, et al., *Cancer Research*, 52:3401–3408, 1992). The increased penetration of Fab also lends itself to potential topical applications. In the case of herpes this may take the form of an antibody cream to treat skin lesions, or as eyedrops for corneal infections. Moreover, the use of a Fab may avoid inflammation arising from activation of effector mechanisms.

EXAMPLE 5

Direct Antigen Capture

A specific mouse monoclonal antibody that binds herpes simplex glycoprotein D (Mab 1103) was utilized as the capture antibody bound to the solid support (obtained from Goodwin Institute for Cancer Research, Plantation, Fla.). The capture antibody was diluted 1:1000 in 0.1 M sodium bicarbonate buffer, pH 8.6 and used to coat ELISA plates (Costar 3690) using 25 µl per well.

Viral protein extracts were obtained by homogenizing HSV-2-infected Vero cells in 1% NP-40, 1% sodium deoxycholate in PBS (I.P. buffer). $10^7$ cells infected with HSV-2 strain G (ATCC VR-734, Rockville, Md.) at a multiplicity of infection (m.o.i.) of 5, were homogenized in 5 ml of I.P. buffer by vortexing. The cell extracts were then sonicated and centrifuged at 3000×g for 5 minutes to remove debris. Cell extracts were then aliquotted and frozen at −80° C. until needed.

Antibody coated plates were repeatedly washed with water and blocked with 3% bovine serum albumin (BSA) in PBS for two hours at 37° C. The BSA solution was then discarded and replaced with 20 µl of the HSV-2-infected cell extracts and incubated at room temperature for 20 minutes. The plates were then washed ten times with PBS containing 0.05% Tween 20. At this point, about $10^{11}$ C.F.U./well of an antibody library (patient AC; as described above) were added and incubated for 1 hour at 37° C. as previously described (Barbas, et al., *Proc. Natl. Acad. Sci. USA*, 88:7978, 1991.; Williamson, et al., *Proc. Natl. Acad. Sci. USA*, 90:4141, 1993). The library suspension was then removed and plates were washed with PBS, 0.05 Tween 20. Bound phage was eluted with 50 µl of 0.1 M HCl adjusted to pH 2.2 with solid glycine.

The eluted phage suspension was immediately neutralized with 3 µl of 2 M Tris base and used to inoculate 2 ml of X-L1 Blue *E. coli* cells (O.D.$_{600}$=0.5). After 15 minutes at room temperature, 10 ml of SB broth containing 20 µg/ml carbenicillin and 10 µg/ml tetracycline were added and the cultures were shaken at 37° C. for one hour. One hundred milliliters of SB containing 50 µg/ml carbenicillin and 10 µg/ml tetracycline were then added and the cultures were shaken for one more hour until $10^{12}$ p.f.u. of helper phage, VCS-M13, were added. After two more hours of shaking, kanamycin was added at a final concentration of 70 µg/ml. The cultures were then shaken overnight at 30 ° C. The next day, phage was prepared after 4 or 5 rounds of panning by a NheI-SpeI restriction enzyme cut followed by self ligation of the vector, as previously described. This removes the portion of phage coat protein III, which anchors the Fabs to the phage particles, from the C-terminus of the heavy chain sequence.

The clones obtained were characterized by immunoprecipitation, neutralization, and DNA sequencing as previously described (Burioni, et al., *Proc. Natl. Acad. Sci. USA*, 91:355, 1994). Some of the clones were identified as AC8 (ATCC 69522) as previously identified neutralizing antibody specific for glycoprotein gD (Burioni, et al., supra).

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:
      (B) CLONE: N1

(ix) FEATURE:
      (A) NAME/KEY: CDS
      (B) LOCATION: 1..32

(xi) SEQUENCE DESCRIPTION: SEQ ID NO:1:

GGCCGCAAAT TCTATTTCAA GGAGACAGTC AT      32

(2) INFORMATION FOR SEQ ID NO:2:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:

(B) CLONE: N2

(ix) FEATURE:
            (A) NAME/KEY: CDS
            (B) LOCATION: 1..36

(xi) SEQUENCE DESCRIPTION: SEQ ID NO:2:

AATGAAATAC CTATTGCCTA CGGCAGCCGC TGGATT                      36

(2) INFORMATION FOR SEQ ID NO:3:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: N3

(ix) FEATURE:
            (A) NAME/KEY: CDS
            (B) LOCATION: 1..32

(xi) SEQUENCE DESCRIPTION: SEQ ID NO:3:

GTTATTACTC GCTGCCCAAC CAGCCATGGC CC                          32

(2) INFORMATION FOR SEQ ID NO:4:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: N6

(ix) FEATURE:
            (A) NAME/KEY: CDS
            (B) LOCATION: 1..29

(xi) SEQUENCE DESCRIPTION: SEQ ID NO:4:

CAGTTTCACC TGGGCCATGG CTGGTTGGG                              29

(2) INFORMATION FOR SEQ ID NO:5:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: N7

(ix) FEATURE:
            (A) NAME/KEY: CDS
            (B) LOCATION: 1..40

(xi) SEQUENCE DESCRIPTION: SEQ ID NO:5:

CAGCGAGTAA TAACAATCCA GCGGCTGCCG TAGGCAATAG                  40

(2) INFORMATION FOR SEQ ID NO:6:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: N8

(ix) FEATURE:
       (A) NAME/KEY: CDS
       (B) LOCATION: 1..38

(xi) SEQUENCE DESCRIPTION: SEQ ID NO:6:

GTATTTCATT ATGACTGTCT CCTTGAAATA GAATTTGC                                    38

(2) INFORMATION FOR SEQ ID NO:7:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: N9-4

(ix) FEATURE:
       (A) NAME/KEY: CDS
       (B) LOCATION: 1..40

(xi) SEQUENCE DESCRIPTION: SEQ ID NO:7:

AGGTGAAACT GCTCGAGATT TCTAGACTAG TTACCCGTAC                                  40

(2) INFORMATION FOR SEQ ID NO:8 :

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: N10-5

(ix) FEATURE:
       (A) NAME/KEY: CDS
       (B) LOCATION: 1..38

(xi) SEQUENCE DESCRIPTION: SEQ ID NO:8 :

CGGAACGTCG TACGGGTAAC TAGTCTAGAA ATCTCGAG                                    38

(2) INFORMATION FOR SEQ ID NO:9 :

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: N11

(ix) FEATURE:
       (A) NAME/KEY: CDS (B) LOCATION: 1..33

(xi) SEQUENCE DESCRIPTION: SEQ ID NO:9 :

GACGTTCCGG ACTACGGTTC TTAATAGAAT TCG                                    33

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: N12

(ix) FEATURE:
        (A) NAME/KEY: CDS
        (B) LOCATION: 1..28

(xi) SEQUENCE DESCRIPTION: SEQ ID NO:10:

TCGACGAATT CTATTAAGAA CCGTAGTC                                          28

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..34

(xi) SEQUENCE DESCRIPTION: SEQ ID NO:11:

TGAATTCTAA ACTAGTCGCC AAGGAGACAG TCAT                                   34

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..36

(xi) SEQUENCE DESCRIPTION: SEQ ID NO:12:

AATGAAATAC CTATTGCCTA CGGCAGCCGC TGGATT                                 36

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS (B) LOCATION: 1..31

(xi) SEQUENCE DESCRIPTION: SEQ ID NO:13:

GTTATTACTC GCTGCCCAAC CAGCCATGGC C                              31

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..30

(xi) SEQUENCE DESCRIPTION: SEQ ID NO:14:

GAGCTCGTCA GTTCTAGAGT TAAGCGGCCG                                30

(2) INFORMATION FOR SEQ ID NO:15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..48

(xi) SEQUENCE DESCRIPTION: SEQ ID NO:15:

CTATTTCATT ATGACTGTCT CCTTGGCGAC TAGTTTAGAA TTCAAGCT            48

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..40

(xi) SEQUENCE DESCRIPTION: SEQ ID NO:16:

CAGCGAGTAA TAACAATCCA GCGGCTGCCG TAGGCAATAG                     40

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..27

(xi) SEQUENCE DESCRIPTION: SEQ ID NO:17:

```
TGACGAGCTC GGCCATGGCT GGTTGGG                                              27

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..24

(xi) SEQUENCE DESCRIPTION: SEQ ID NO:18:

TCGACGGCCG CTTAACTCTA GAAC                                                 24

(2) INFORMATION FOR SEQ ID NO:19:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..48

(xi) SEQUENCE DESCRIPTION: SEQ ID NO:19:

GAGACGACTA GTGGTGGCGG TGGCTCTCCA TTCGTTTGTG AATATCAA                       48

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..40

(xi) SEQUENCE DESCRIPTION: SEQ ID NO:20:

TTACTAGCTA GCATAATAAC GGAATACCCA AAAGAACTGG                                40

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..36

(xi) SEQUENCE DESCRIPTION: SEQ ID NO:21:

TATGCTAGCT AGTAACACGA CAGGTTTCCC GACTGG                                    36
```

-continued (2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..27

(xi) SEQUENCE DESCRIPTION: SEQ ID NO:22:

ACCGAGCTCG AATTCGTAAT CATGGTC        27

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..31

(xi) SEQUENCE DESCRIPTION: SEQ ID NO:23:

AGCTGTTGAA TTCGTGAAAT TGTTATCCGC T        31

The foregoing is meant to illustrate, but not to limit, the scope of the invention. Indeed, those of ordinary skill in the art can readily envision and produce further embodiments, based on the teachings herein, without undue experimentation.

What is claimed is:

1. method for obtaining a second antibody that binds to a previously unknown epitope on a preselected antigen, comprising:
    a) forming an immunocomplex by contacting the preselected antigen with a first antibody bound to a solid support, wherein the first antibody specifically binds to a preselected epitope present on the preselected antigen;
    b) contacting the immunocomplex of a) with a combinatorial library of antibodies under conditions that allow binding of the second antibody to the previously unknown epitope, wherein the second antibody is obtained from screening the combinatorial library;
    c) removing the second antibody of b) from the previously unknown epitope; and
    d) obtaining the second antibody.

2. The method of claim 1, wherein the first antibody is an Fv or an Fab fragment.

3. The method of claim 1, wherein the first antibody is a monoclonal antibody.

4. The method of claim 1, wherein the antigen is selected from the group consisting of a bacterial, a viral, a parasitic, a fungal, a tumor and a self-antigen.

5. The method of claim 4, wherein the viral antigen is selected from the group of viruses consisting of a hepatitis B virus (HBV), a human immunodeficiency virus (HIV), an influenza A virus, an Epstein Barr virus (EBV), a herpes simplex virus (HSV), a respiratory syncytial virus (RSV), a human cytomegalovirus (HCMV), a varicella zoster virus (VZV), and a measles virus.

6. The method of claim 5, wherein the viral antigen is a HSV glycoprotein D.

7. The method of claim 1, wherein the preselected epitope is a non-neutralizing epitope.

8. The method of claim 1, wherein the previously unknown epitope is a neutralizing epitope.

9. The method of claim 1, further comprising the step of sequencing a nucleic acid encoding an amino acid sequence of the second antibody.

\* \* \* \* \*

UNITED STATES PATENT AND TRADEMARK OFFICE
CERTIFICATE OF CORRECTION

PATENT NO. : 6,376,170 B1 Page 1 of 1
DATED : April 23, 2002
INVENTOR(S) : D. Burton et al.

It is certified that error appears in the above-identified patent and that said Letters Patent is hereby corrected as shown below:

<u>Column 1,</u>
Please insert the following:

-- This invention was made with government support under Contract Nos. AI 33292 and AI 35165 by the National Institutes of Health. The government has certain rights in this invention. --

Signed and Sealed this

Third Day of December, 2002

JAMES E. ROGAN
*Director of the United States Patent and Trademark Office*